United States Patent
Toyoshima et al.

(10) Patent No.: US 9,856,304 B2
(45) Date of Patent: Jan. 2, 2018

(54) PEPTIDE AND APPLICATION THEREOF

(71) Applicant: Saitama Medical University, Iruma-gun, Saitama (JP)

(72) Inventors: Hideo Toyoshima, Saitama (JP); Yasushi Okazaki, Saitama (JP); Tomotaka Yokoo, Saitama (JP); Izumi Sugahara, Saitama (JP)

(73) Assignee: SAITAMA MEDICAL UNIVERSITY, Saitama (JP)

( * ) Notice: Subject to any disclaimer, the term of this patent is extended or adjusted under 35 U.S.C. 154(b) by 0 days.

(21) Appl. No.: 14/893,730

(22) PCT Filed: May 23, 2014

(86) PCT No.: PCT/JP2014/063674
§ 371 (c)(1),
(2) Date: Nov. 24, 2015

(87) PCT Pub. No.: WO2014/189127
PCT Pub. Date: Nov. 27, 2014

(65) Prior Publication Data
US 2016/0311875 A1    Oct. 27, 2016

(30) Foreign Application Priority Data
May 24, 2013   (JP) ................. 2013-109801

(51) Int. Cl.
| C07K 14/00 | (2006.01) |
| C07K 14/62 | (2006.01) |
| A61K 38/16 | (2006.01) |
| C12N 5/00 | (2006.01) |
| C12N 5/071 | (2010.01) |
| C07K 14/475 | (2006.01) |
| A61K 38/00 | (2006.01) |
| C07K 14/705 | (2006.01) |

(52) U.S. Cl.
CPC ............ *C07K 14/475* (2013.01); *A61K 38/00* (2013.01); *C07K 14/705* (2013.01); *C12N 5/0676* (2013.01); *C12N 2501/998* (2013.01); *C12N 2506/45* (2013.01)

(58) Field of Classification Search
None
See application file for complete search history.

(56) References Cited

U.S. PATENT DOCUMENTS

| 9,139,647 B2 * | 9/2015 | Aburatani | C07K 16/28 |
| 2010/0168026 A1 | 7/2010 | Toyoshima et al. | |
| 2012/0004117 A1 * | 1/2012 | Aburatani | C07K 16/28 506/7 |

FOREIGN PATENT DOCUMENTS

| EP | 2168589 A1 | 3/2010 |
| JP | 2007209214 A | 8/2007 |
| WO | 2005063971 A2 | 7/2005 |
| WO | 2006108361 A1 | 10/2006 |
| WO | 207051038 A2 | 5/2007 |
| WO | 2007103282 A2 | 9/2007 |
| WO | 2008066199 A1 | 6/2008 |
| WO | 2009013794 A1 | 1/2009 |
| WO | 2009048675 A1 | 4/2009 |

OTHER PUBLICATIONS

Wells, Additivity of Mutational Effects in Proteins. Biochemistry 29:8509-8517 (1990).*
Tokuriki, Stability effects of mutations and protein evolvability. Current Opinion in Structural Biology, 19:596-604 (2009).*
D'Amour, K. A. et al., "Production of pancreatic hormone-expressing endocrine cells from human embryonic stem cells", Nature Biotechnology, 2006 Nature Publishing Group, 24, pp. 1392-1401.
Hideo Toyoshima et al., "Shokakan Hormone IBCAP ni yoru Sui β Saibo Bunka Zoshoku ni Ataeru Eikyo", Folia endocrinologica Japonica, Apr. 1, 2013 (Apr. 1, 2013), vol. 89, No. 1, p. 270, Impact on Differentiation and Proliferation of Pancreas Beta-Cells by Gastrointestinal Hormone IBCAP-P1-12-1.
International Search Report corresponding to Application No. PCT/JP2014/063674; dated Aug. 26, 2014, with English translation.
Miyazaki, S. et al., "Regulated Expression of pds-1 Promotes In Vitro Differentiation of Insulin-Producing Cells From Embryonic Stem Cells", Diabetes, vol. 53, Apr. 2004, pp. 1030-1037.
Tomotaka Yokoo et al., "Shinki Shokakan Hormone IBCAP ni yoru Sui β Saibo Bunka Zoshoku Sayo no Kaiseki", The Journal of the Japan Diabetic Society, Apr. 25, 2013 (Apr. 25, 2013), vol. 56, Supplement 1, p. S-198, Analysis of Differentiation/Proliferation Activity of Pancreas Beta-Cells by New Gastrointestinal Hormone IBCAP—1-P-422.
Wei Jiang et al., "In vitro derivation of functional insulin-producing cells from human embryonic stem cells", Cell Research (2007) 17, pp. 333-344.
Yuya Kunisada et al., "Small molecules induce efficient differentiation into insulin-producing cells from human induced pluripotent stem cells", Stem Cell Research (2012) 8, pp. 274-284.
"Abstracts of the EASD, Stockholm 2010; held in Messe Wien, Vienna, Austria on Oct. 1, 2009", Diabetologia; Clinical and Experimental Diabetes and Metabolism, Springer, Berlin, DE, vol. 53, No. 1, Aug. 6, 2010 (Aug. 6, 2010), pp. 1-556, XP019836294.
Extended European search report for European Patent Application No. 14801460.8 dated Nov. 2, 2016.
Yokoo Tomotaka et al: "Identification of CF266, a novel intestine-specific secretory protein with incretin-like activity", Diabetes, American Diabetes Association, US, vol. 57, No. Suppl. 1, Jun. 10, 2008 (Jun. 10, 2008), pp. A446-A447, XP009135326.

* cited by examiner

Primary Examiner — Elizabeth C Kemmerer
Assistant Examiner — Regina M Deberry
(74) Attorney, Agent, or Firm — Cantor Colburn LLP

(57) ABSTRACT

Provided are a new peptide, a vector inserting a DNA that codes said peptide, a transformant obtained by transformation with that vector, and applications of said peptide, vector and transformant. The peptide comprises an amino acid sequence set forth in SEQ ID NO: 1, or an amino acid sequence obtained by substituting, deleting or adding one or more amino acids to/from the amino acid sequence set forth in SEQ ID NO: 1. This peptide and the vector inserting a DNA that codes this peptide are suitable for use in an agent for promoting the proliferation of pancreatic hormone-producing cells, or a differentiation induction promoter that induces differentiation to pancreatic hormone-producing cells.

6 Claims, 6 Drawing Sheets

PEPTIDE AND APPLICATION THEREOF

TECHNICAL FIELD

The present invention relates to a novel peptide, a vector inserting a DNA that encodes the peptide, a transformant transformed with the vector and use thereof.

BACKGROUND ART

The pancreas is an organ which has endocrine and exocrine cells and plays an important role in both internal and external secretions. It is known that endocrine cells serve to produce and secret pancreatic hormones, and α cells, β cells, δ cells and PP cells secrete glucagon, insulin, somatostatin and pancreatic polypeptides, respectively. In particular, insulin has an activity for decreasing a blood sugar level, and plays an important role in maintaining a blood sugar level at the normal concentration.

In recent years, a polypeptide known as human TM4SF20 or a fragment thereof has been reported to have an activity for promoting increase in pancreatic β cells (see Patent Document 1). The base sequence of a DNA that encodes human TM4SF20 is set forth in SEQ ID NO: 2, and the amino acid sequence of human TM4SF20 is set forth in SEQ ID NO: 3. This polypeptide or a fragment thereof can potentially be used for treating diseases associated with decrease or death of pancreatic β cells, in particular, for treating Type I diabetes mellitus.

However, the polypeptide (human TM4SF20) described in Patent Document 1 comprises 229 amino acid residues, and thus a peptide with a shorter the length of amino acid residues is desired for practical use. Although Patent Document 1 also describes 3 fragments (Peptides A, B, C) comprising 19 amino acid residues as a peptide with a shorter length of amino acid residues, the activity for promoting increase in pancreatic β cells was not as high as expected. The amino acid sequences of Peptides A, B, C are set forth in SEQ ID NOs: 4 to 6, respectively. Note that the amino acid sequences of Peptides A, B, C correspond to the amino acid sequences from Position 98 to 116, from Position 78 to 96 and from Position 161 to 179 of human TM4SF20, respectively.

Further, in recent years, pluripotent stem cells such as induced pluripotent stem cells (hereinafter also referred to as "iPS cells") and embryonic stem cells (hereinafter also referred to as "ES cells"), or many methods for inducing differentiation of pancreas tissue stem/precursor cells into pancreatic hormone-producing cells have been reported (see Nonpatent Documents 1 to 4, Patent Documents 2 to 7 and the like). If pancreatic hormone-producing cells can be efficiently obtained by these differentiation-inducing methods, a method of treating Type I diabetes mellitus is expected to become a substitute for pancreatic islet transplantation. Furthermore, the problem of rejection can also be solved if pancreatic hormone-producing cells can be obtained from pluripotent stem cells or pancreas tissue stem/precursor cells derived from a patient himself/herself.

However, none of the differentiation-inducing methods reported to date has a sufficient differentiation-inducing efficiency into pancreatic hormone-producing cells. Accordingly, a differentiation-inducing method capable of high efficiency inducing differentiation into pancreatic hormone-producing cells has been desired. In particular, a differentiation-inducing method without a gene transfer is preferred in view of safety.

Patent Document 1: PCT International Publication No. WO2009/013,794
Patent Document 2: PCT International Publication No. WO2007/103,282
Patent Document 3: PCT International Publication No. WO2005/063,971
Patent Document 4: PCT International Publication No. WO2009/048,675
Patent Document 5: PCT International Publication No. WO2007/051,038
Patent Document 6: PCT International Publication No. WO2006/108,361
Patent Document 7: PCT International Publication No. WO2008/066,199
Non-Patent Document 1: D'Amour, K. A. et al., Nature Biotechnology, 24, pp. 1392-1401(2006)
Non-Patent Document 2: Wei Jiang et al., Cell Research, 17, pp. 333-344(2007)
Non-Patent Document 3: Miyazaki, S. et al., Diabetes, 53, pp. 1030-1037(2004)
Non-Patent Document 4: Yuya Kunisada et al., Stem Cell Research, 8, pp. 274-284(2012)

DISCLOSURE OF THE INVENTION

Problems to be Solved by the Invention

An object of the present invention is to provide a novel peptide, a vector inserting a DNA that encodes the peptide, a transformant transformed with the vector and use thereof.

Means for Solving the Problems

The present inventors conducted extensive studies in view of the above object. As a result, the present inventors find that a peptide, which is a fragment of human TM4SF20, consisting of the amino acid sequence set forth in SEQ ID NO: 1 (hereinafter also referred to as "betagenin") has a high growth-promoting activity for pancreatic hormone-producing cells, and a high differentiation induction promoting activity into pancreatic hormone-producing cells. The present invention has been completed based on these findings. More specifically, it is described as follows.

[1] A peptide consisting of an amino acid sequence set forth in SEQ ID NO: 1, or an amino acid sequence having one or several amino acid substitutions, deletions and/or additions in the amino acid sequence set forth in SEQ ID NO: 1.

[2] A vector inserting a DNA that encodes the peptide according to the above [1].

[3] A research reagent comprising the peptide according to the above [1] or the vector according to the above [2].

[4] The research reagent according to the above [3], which is a pancreatic hormone-producing cell growth-promoting agent for promoting the growth of pancreatic hormone-producing cells and/or a differentiation-induction promoting agent for inducing differentiation into pancreatic hormone-producing cells.

[5] The research reagent according to the above [4], wherein the pancreatic hormone-producing cells comprise at least one selected from the group consisting of α cells, β cells and δ cells.

[6] A pharmaceutical composition comprising the peptide according to the above [1] or the vector according to the above [2].

[7] A transformant transformed with the vector according to the above [2].

3

[8] A method of producing a peptide, comprising a step of culturing the transformant according to the above [7] to produce the peptide according to the above [1].

[9] A pancreatic hormone-producing cell growth-promoting agent for promoting the growth of pancreatic hormone-producing cells, comprising at least one of the following (a) to (c);
- (a) a peptide consisting of the amino acid sequence set forth in SEQ ID NO: 1,
- (b) a peptide consisting of an amino acid sequence having one or several amino acid substitutions, deletions and/or additions in the amino acid sequence set forth in SEQ ID NO: 1, and having a growth-promoting activity for pancreatic hormone-producing cells,
- (c) a vector inserting a DNA that encodes the peptide according to the above (a) or (b).

[10] A differentiation-induction promoting agent for inducing differentiation into pancreatic hormone-producing cells, comprising at least one of the following (d) to (f);
- (d) a peptide consisting of the amino acid sequence set forth in SEQ ID NO: 1,
- (e) a peptide consisting of an amino acid sequence having one or several amino acid substitutions, deletions and/or additions in the amino acid sequence set forth in SEQ ID NO: 1, and having a differentiation induction promoting activity into pancreatic hormone-producing cells,
- (f) a vector inserting a DNA that encodes the peptide according to the above (d) or (e).

[11] A method of proliferating pancreatic hormone-producing cells, the method comprising a step of adding a peptide according to the following (a) or (b) to a culture medium for culturing the pancreatic hormone-producing cells;
- (a) a peptide consisting of the amino acid sequence set forth in SEQ ID NO: 1,
- (b) a peptide consisting of an amino acid sequence having one or several amino acid substitutions, deletions and/or additions in the amino acid sequence set forth in SEQ ID NO: 1, and having a growth-promoting activity for pancreatic hormone-producing cells.

[12] A method of differentiation-formation into pancreatic hormone-producing cells, the method comprising a step of adding a peptide according to the following (d) or (e) to a culture medium in the course of a differentiation induction process of pluripotent stem cells or pancreas tissue stem/precursor cells into pancreatic hormone-producing cells;
- (d) a peptide consisting of the amino acid sequence set forth in SEQ ID NO: 1,
- (e) a peptide consisting of an amino acid sequence having one or several amino acid substitutions, deletions and/or additions in the amino acid sequence set forth in SEQ ID NO: 1, and having a differentiation induction promoting activity into pancreatic hormone-producing cells.

[13] A method of forming a cluster of pancreatic hormone-producing cells for regeneration medicine, comprising the proliferation method according to the above [11] and/or the differentiation-formation method according to the above [12].

[14] The formation method according to the above [13], wherein the above cluster of pancreatic hormone-producing cells comprises α cells or β cells.

Effects of the Invention

The present invention can provide a novel peptide, a recombinant vector inserting a DNA that encodes the peptide, a transformant transformed with the recombinant vector and use thereof.

PREFERRED MODE FOR CARRYING OUT THE INVENTION

Peptide

Figure 1:
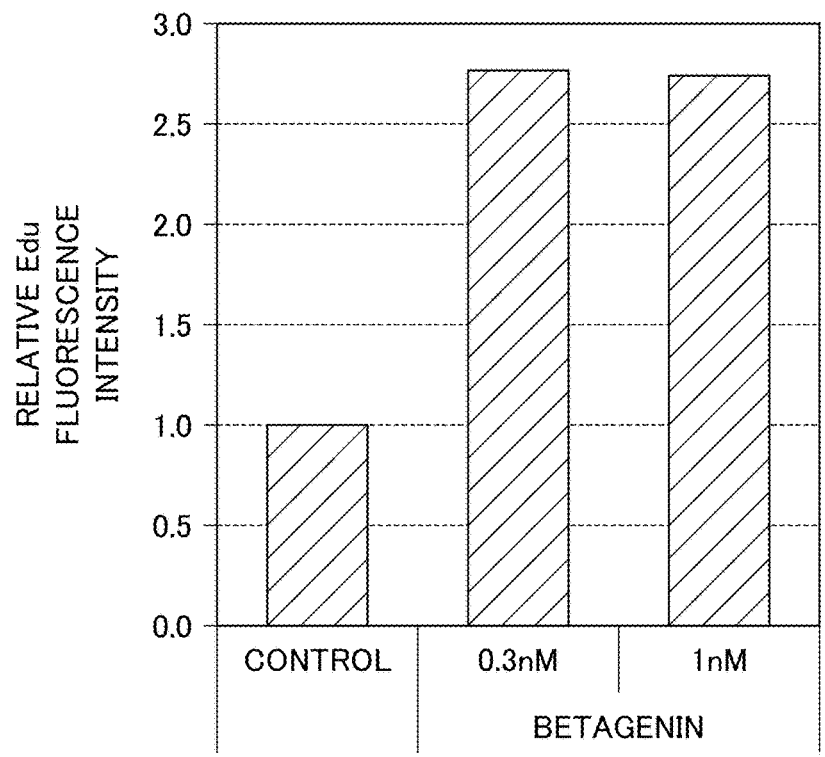
FIG. 1 shows growth-promoting activities for a pancreatic β cell line when the peptide (betagenin) consisting of the amino acid sequence set forth in SEQ ID NO: 1 was added to a culture medium.

The peptide according to the present invention consists of the amino acid sequence set forth in SEQ ID NO: 1 or an amino acid sequence having one or several amino acid substitutions, deletions and/or additions in the amino acid sequence set forth in SEQ ID NO: 1.

The amino acid sequence set forth in SEQ ID NO: 1 corresponds to an amino acid sequence of human TM4SF20 from Position 170 to Position 229. As described below, the peptide consisting of the amino acid sequence set forth in SEQ ID NO: 1 has a high growth-promoting activity for pancreatic hormone-producing cells and a differentiation induction promoting activity into pancreatic hormone-producing cells. Note that pancreatic hormone-producing cells usually comprise at least one selected from the group consisting of α cells, β cells and δ cells.

The peptide according to the present invention encompasses a peptide consisting of an amino acid sequence having one or several amino acid substitutions, deletions and/or additions in the amino acid sequence set forth in SEQ ID NO: 1 (hereinafter also referred to as a "modified peptide"). It is a widely known fact for one of ordinary skill in the art that a peptide consisting of an amino acid sequence having one or several amino acid substitutions, deletions and/or additions in a certain amino acid sequence can maintain the biological activity of the original peptide (for example, see Mark, D. F. et al., Proc. Natl. Acad. Sci. USA, 81, pp. 5662-5666 (1984); Zoller, M. J. et al., Nucleic Acids Research, 10, pp. 6487-6500 (1982); Wang, A. et al., Science, 224, pp. 1431-1433; Dalbadie-McFarland, G. et al., Proc. Natl. Acad. Sci. USA, 79, pp. 6409-6413 (1982)).

In this context, in a case where one or several amino acids are substituted with other amino acids, the properties of amino acid side chains are preferably conserved before and after substitution. The properties of amino acid side chains include hydrophobic amino acids (A, I, L, M, F, P, W, Y, V), hydrophilic amino acids (R, D, N, C, E, Q, G, H, K, S, T), amino acids having an aliphatic side chain (G, A, V, L, I, P), amino acids having a hydroxy group-containing side chain (S, T, Y), amino acids having a sulfur atom-containing side chain (C, M), amino acids with a side chain having carboxylic acid or amide (D, N, E, Q), amino acids having a base-containing side chain (R, K, H), amino acids having an aromatic-containing side chain (H, F, Y, W) (each of the alphabetical letters in parenthesis represents the one-letter notation for amino acids).

In a case where one or several amino acids are substituted, deleted and/or added, the number thereof may be, for example, 1 to 12, or may be 1 to 6, or may be 1 to 4, or may be 1 to 2.

Further, the homology between a modified peptide and the original peptide is preferably 80% or more, more preferably 90% or more, even more preferably 93% or more, in particular preferably 95% or more, and most preferably 98% or more.

Vector

A vector according to the present invention inserts a DNA that encodes the peptide according to the present invention. A plasmid vector, a phage vector, a retroviral vector, an adenoviral vector, an adeno-associated viral vector and the like may be used as a vector, which is appropriately selected depending on the intended use.

Research Reagent and Pharmaceutical Composition

The research reagent according to the present invention comprises the peptide according to the present invention or the vector according to the present invention. The research reagent may be a pancreatic hormone-producing cell growth-promoting agent described below, or may be a differentiation-induction promoting agent described below, or may be the both. The research reagent can suitably be used for studies in which pancreatic hormone-producing cells are used; studies of the differentiation mechanism into pancreatic hormone-producing cells; and the like.

Further, the pharmaceutical composition according to the present invention comprises the peptide according to the present invention or the vector according to the present invention. As described below, the peptide consisting of the amino acid sequence set forth in SEQ ID NO: 1 can show an excellent growth-promoting activity for pancreatic hormone-producing cells and a differentiation induction promoting activity into pancreatic hormone-producing cells. Therefore, the pharmaceutical composition can be used, for example, for the treating diseases associated with death or decrease of pancreatic β cells, in particular for treating Type I diabetes mellitus. For example, the peptide according to the present invention can be formulated into a pharmaceutical composition by a known method, which can be administered to a patient. Further, the vector according to the present invention can be formulated into a pharmaceutical composition by a known method, which can be administered to a patient.

Transformant and Method of Producing Peptide

The transformant according to the present invention is one transformed with the vector according to the present invention. Further, a method of producing the peptide according to the present invention comprises a step of culturing the transformant according to the present invention to produce the peptide according to the present invention.

There is no particular limitation for host cells as long as they are compatible and transformable with a transforming vector. Specific examples thereof include bacteria, yeast, insect cells, animal cells and the like.

By culturing the transformant to allow gene expression, the peptide according to the present invention can be obtained from the culture supernatant thereof. Separation and purification of the peptide can be performed by a method commonly used in peptide chemistry, for example, an ion exchange resin, partition chromatography, gel filtration chromatography, reversed phase chromatography and the like.

Note that, of course, the peptide according to the present invention can also be obtained by chemical synthesis.

Pancreatic Hormone-Producing Cell Growth-Promoting Agent

The pancreatic hormone-producing cell growth-promoting agent according to the present invention comprises at least one of the following (a) to (c), and is capable of promoting the growth of pancreatic hormone-producing cells.

(a) a peptide consisting of the amino acid sequence set forth in SEQ ID NO: 1,
(b) a peptide consisting of an amino acid sequence having one or several amino acid substitutions, deletions and/or additions in the amino acid sequence set forth in SEQ ID NO: 1, and having a growth-promoting activity for pancreatic hormone-producing cells,
(c) a vector inserting a DNA that encodes the peptide according to the above (a) or (b).

The peptide consisting of the amino acid sequence set forth in SEQ ID NO: 1 has a high growth-promoting activity for pancreatic hormone-producing cells. Therefore, this peptide can be used for a pancreatic hormone-producing cell growth-promoting agent.

Further, a modified peptide consisting of an amino acid sequence having one or several amino acid substitutions, deletions and/or additions in the amino acid sequence set forth in SEQ ID NO: 1 can also be used as long as a growth-promoting activity for pancreatic hormone-producing cells is retained. The number of amino acids to be substituted, deleted and/or added, and the homology between the modified peptide and the original peptide may be similar to those described for the peptide according to the present invention.

Further, a vector inserting a DNA that encodes the peptide according to the above (a) or (b) can also be used as a pancreatic hormone-producing cell growth-promoting agent.

A peptide and a vector as an active ingredient may be used alone in a pure form highly purified, or may be used in combination of two or more.

The pancreatic hormone-producing cell growth-promoting agent according to the present invention can show an excellent growth-promoting activity for pancreatic hormone-producing cells. Therefore, the above growth-promoting agent can be used, for example, for treating diseases associated with death or decrease of pancreatic β cells, in particular for treating Type I diabetes mellitus.

For example, a pharmaceutical composition which can be obtained by formulating the peptide according to the above (a) or (b) by a conventionally known method can be administered to a patient.

Further, a pharmaceutical composition which can be obtained by inserting a DNA that encodes the peptide according to the above (a) or (b) into an appropriate vector (a retroviral vector, an adenoviral vector, an adeno-associated viral vector and the like) and performing formulation by a conventionally known method can be administered to a patient.

Method of Proliferating Pancreatic Hormone-Producing Cells

A proliferation method according to the present invention comprises a step of adding the peptide according to the above (a) or (b) to a culture medium for culturing pancreatic hormone-producing cells. The proliferation of pancreatic hormone-producing cells is promoted by adding the above (a) or (b) as described above. The concentration of the peptide in a culture medium is preferably 0.03 to 10 nM, more preferably 0.3 to 1 nM.

Differentiation-Induction Promoting Agent

The differentiation-induction promoting agent according to the present invention comprises at least one of following (d) to (f), and is capable of inducing differentiation into pancreatic hormone-producing cells.

(d) a peptide consisting of the amino acid sequence set forth in SEQ ID NO: 1,
(e) a peptide consisting of an amino acid sequence having one or several amino acid substitutions, deletions and/or additions in the amino acid sequence set forth in SEQ ID NO: 1, and having a differentiation induction promoting activity into pancreatic hormone-producing cells,
(f) a vector inserting a DNA that encodes the peptide according to the above (d) or (e).

The peptide consisting of the amino acid sequence set forth in SEQ ID NO: 1 has an activity for promoting differentiation induction of pluripotent stem cells as well as tissue stem/precursor cells such as pancreas tissue stem/precursor cells into pancreatic hormone-producing cells. Therefore, this peptide can be used for a differentiation-induction promoting agent.

Further, a modified peptide consisting of an amino acid sequence having one or several amino acid substitutions, deletions and/or additions in the amino acid sequence set forth in SEQ ID NO: 1 can also be used as long as the differentiation induction promoting activity into pancreatic hormone-producing cells is retained. The number of amino acids to be substituted, deleted and/or added, and the homology between a modified peptide and the original peptide may be similar to those described for the peptide according to the present invention.

Further, a vector inserting a DNA that encodes the peptide according to the above (d) or (e) can also be used for a differentiation-induction promoting agent.

A peptide and a vector as an active ingredient may be used alone in a pure form highly purified, or may be used in combination of two or more.

Note that pluripotent stem cells refer to self-replicable stem cells having an ability (multilineage potential) of differentiating into differentiated cells belonging to at least each one of triploblastics (ectoderm, mesoderm, endoderm), including, for example, induced pluripotent stem cells (iPS cells), embryonic stem cells (ES cells), embryonic germ cells (EG cells), embryonic cancer cells (EC cells), adult pluripotent stem cells (APS cells) and the like.

Further, tissue stem/precursor cells are the stem/precursor cells that have multilineage potential and self-replication capability, and are present in the living body.

The differentiation-induction promoting agent according to the present invention can show a differentiation induction promoting activity into pancreatic hormone-producing cells. Therefore, the above differentiation-induction promoting agent can be used for treating, for example, diseases associated with death or decrease of pancreatic β cells, in particular Type I diabetes mellitus.

For example, the peptide according to the above (d) and (e) can be formulated by a conventionally known method, which can then be administered to a patient.

Further, a DNA that encodes the peptide according to the above (d) or (e) can be incorporated into an appropriate vector (a retroviral vector, an adenoviral vector, an adeno-associated viral vector and the like), which can then be formulated by a conventionally known method and administered to a patient.

Further, the differentiation-induction promoting agent according to the present invention can also be used when inducing differentiation of pluripotent stem cells or pancreas tissue stem/precursor cells into pancreatic hormone-producing cells.

For example, the differentiation of pluripotent stem cells or pancreas tissue stem/precursor cells into pancreatic hormone-producing cells can be induced by adding the peptide according to the above (d) and (e) to a culture medium.

Method of Differentiation-Formation of Pancreatic Hormone-Producing Cells

The differentiation-formation method according to the present invention comprises a step of adding the peptide according to the above (d) or (e) to a culture medium in the course of a differentiation induction process of pluripotent stem cells or pancreas tissue stem/precursor cells into pancreatic hormone-producing cells. Below, the differentiation-formation method will further be described.

Differentiation-Induction of Pluripotent Stem Cells into Pancreatic Hormone-Producing Cells In order to induce the differentiation of pluripotent stem cells into pancreatic hormone-producing cells, the peptide according to the above (d) or (e) may be added to a culture medium in the course of the differentiation induction process. There is no particular limitation for a method of inducing the differentiation of pluripotent stem cells into pancreatic hormone-producing cells, and any conventionally known method can be used. The concentration of the peptide according to the above (d) or (e) in a culture medium is preferably 10 to 200 ng/mL, more preferably 50 to 180 ng/mL, and even more preferably 60 to 150 ng/mL.

Below, two methods will be described as examples of the method of inducing the differentiation of pluripotent stem cells into pancreatic hormone-producing cells, but the method shall not be limited to these.

[First Differentiation Induction Method]

A first differentiation induction method is in accordance with a method described in Nonpatent Document 1. This reference is incorporated herein by reference.

The first differentiation induction method comprises the following steps (A1) to (E1). The peptide according to the above (d) or (e) is added to a culture medium in at least one of these steps. Note that when adding a differentiation-induction promoting agent in a certain step, it may be added at the beginning of the step or may be added at the middle of the step. In particular, the peptide according to the above (d) or (e) is preferably added at all of the steps (A1) to (E1).

(A1) A step of culturing pluripotent stem cells in the presence of a growth factor belonging to the TGF-β superfamily (transforming growth factor β).

(B1) A step of culturing cells obtained at the above step (A1) in the presence of FGF (fibroblast growth factor).

(C1) A step of culturing the cells obtained at the above step (B1) in the presence of retinoid.

(D1) A step of culturing the cell obtained at the above step (C1) in the presence of a γ-secretase inhibitor.

(E1) A step of culturing cells obtained at the above step (D1) in the presence of at least one factor selected from the group consisting of exendin-4, HGF (hepatocyte growth factor), IGF-1 (insulin like growth factor-1) and nicotinamide.

(Step (A1))

At the step (A1), pluripotent stem cells are cultured in the presence of a growth factor belonging to the TGF-β superfamily.

Growth factors belonging to the TGF-β superfamily include activin, nodal, BMP (bone morphogenetic protein) and the like. Among these, activin is preferred. It is known that those growth factors belonging to the TGF-β superfamily can promote differentiation of pluripotent stem cells into embryonic endoderm cells (see Nonpatent Document 1, Patent Documents 2 to 4 and the like). Examples of activin include activin A, activin B, activin AB and the like. Among these, activin A is preferred.

The concentration of a growth factor belonging to the TGF-β superfamily is preferably 5 to 250 ng/mL, more preferably 10 to 200 ng/mL, and even more preferably 50 to 150 ng/mL.

Further, at the step (A1), a growth factor belonging to the Wnt (wingless MMTV integration site) family is preferably added to a culture medium. The differentiation efficiency into embryonic endoderm cells can be increased by adding a growth factor belonging to the Wnt family along with a growth factor belonging to the TGF-β superfamily.

Growth factors belonging to the Wnt family include Wnt1, Wnt3a, Wnt5a, Wnt7a and the like. Wnt1, Wnt3a are preferred, and Wnt3a is more preferred.

The concentration of a growth factor belonging to the Wnt family is preferably 1 to 1000 ng/mL, more preferably 10 to 100 ng/mL, and even more preferably 10 to 50 ng/mL.

Note that at the step (A1), a GSK-3 (glycogen synthase kinase 3) inhibitor (for example, CHIR) may be added instead of a growth factor belonging to the Wnt family. It is known that a GSK-3 inhibitor (for example, CHIR) activates a Wnt signaling pathway (J. Biol. Chem. 277 (34), pp. 30998-31004 (2002)).

Further, at the step (A1), an additional factor which can increase a differentiation efficiency into embryonic endoderm cells may be added to a culture medium. Additional factors include, for example, PDGF (platelet-derived growth factor), EGF (epidermal growth factor), VEGF (vascular endothelial cell growth factor), KGF (keratinocyte growth factor), HGF, NGF (nerve growth factor), GDF (growth differentiation factor), GLP (glucagon-like peptide), nicotinamide, exendin-4, retinoic acid, ethanolamine, parathyroid hormone, progesterone, aprotinin, hydrocortisone, gastrin, steroid alkaloid, copper chelators (triethylene pentamine and the like), forskolin, sodium butyrate, noggin, valproic acid, trichostatin A, Indian hedgehog, Sonic hedgehog, proteasome inhibitors, notch pathway inhibitors, hedgehog pathway inhibitors and the like.

For a container used for culture, preferred is a culture plate coated with a scaffold of a biocompatible material in view of a differentiation induction capability, a functional expression capability, viability and the like. Scaffolds include laminin, fibronectin, collagen, heparan sulphate proteoglycan, gelatin, entactin, polyornithine and the like. MATRIGEL™, Growth factor-reduced MATRIGEL™ from Becton Dickinson and the like are available as commercial products. In particular, a culture plate coated with MATRIGEL™ is preferably used.

A culture medium used for culture may be prepared by adding various nutrient sources and other components required for cell maintenance and proliferation to a basal medium which can be used for culturing animal cells.

Basal media include RPMI1640 culture medium, DMEM culture medium, CMRL1066 culture medium, Ham F12 culture medium, Eagle MEM culture medium, Glasgow MEM culture medium, IMEM Zinc Option culture medium, IMDM culture medium, William E culture medium, Fischer culture medium, McCoy culture medium, BME culture medium, α-MEM culture medium, BGJb culture medium, Medium 199 culture medium, or mixed media thereof and the like.

Nutrient sources include carbon sources such as glycerol, glucose, fructose, sucrose, lactose, starch, dextrin; hydrocarbons such as fatty acid, fats and oils, lecithin, alcohol; nitrogen sources such as ammonium sulfate, ammonium nitrate, ammonium chloride, urea, sodium nitrate; inorganic salts such as sodium salts, potassium salts, magnesium salts, calcium salts, phosphate salts; various vitamins; various amino acids; and the like.

Other components include antibiotics such as penicillin, streptomycin; cholera toxin; insulin; transferrin; selenious acid; albumin; 2-mercaptoethanol; blood serum or blood serum substitutes; and the like. For insulin, transferrin and selenious acid, ITS-X, ITS-A, ITS-G from Invitrogen and the like are available as commercial products. Further, for blood serum substitutes, a B-27™ supplement, an N-2 supplement, a Knockout™ blood serum substitute from Invitrogen and the like are available as commercial products.

Here, in order to increase the differentiation efficiency at the step (A1), it is known that sufficiently low contents of insulin, IGF and the like in a culture medium are important (see WO2006/020919). Therefore, serum-free culture medium or low-serum culture medium is preferably used at the step (A1) (see Nonpatent Document 1, Patent Documents 2 to 4). The serum concentration is preferably 0 to 2% (v/v), more preferably 0 to 1% (v/v), and even more preferably 0 to 0.5% (v/v).

According to a preferred embodiment, used is a serum-free or low-serum RPMI1640 culture medium with added activin A, Wnt 3a, an antibiotic such as penicillin and streptomycin, L-glutamine or a dipeptide including L-glutamine.

The culture period at the step (A1) is, for example, 1 to 6 days, and preferably 2 to 4 days.

The progress of differentiation induction into embryonic endoderm cells can also be evaluated by observing gene expression by RT-PCR in addition to by morphological observation. As the differentiation of pluripotent stem cells into embryonic endoderm cells proceeds, the expression of marker genes for stem cells, OCT4, NANOG, SOX2, ECAD and the like decreases, and the expression of marker genes for embryonic endoderm cells, SOX17, CER, FOXA2, CXCR4 and the like is promoted.

Note that the concentration of blood serum in a culture medium needs to be reduced in order to increase the differentiation efficiency into embryonic endoderm cells while the concentration of blood serum in a culture medium is preferably increased in order to increase of the viability of cells.

Accordingly, the step (A1) is preferably divided into two substeps: a step (A1-1) of performing culture in a first serum-free culture medium and a step (A1-2) of performing culture in a second low-serum culture medium.

The first culture medium used at the step (A1-1) may be similar to the above except that it is serum-free. That is, the first culture medium may contain a growth factor belonging to the TGF-β superfamily, and in addition, may contain a growth factor belonging to the Wnt family. More preferably, the above first culture medium contains a growth factor belonging to the Wnt family.

The culture period at the step (A1-1) is, for example, 1 to 3 days, and preferably 1 to 2 days. The differentiation of pluripotent stem cells into mesendoderm cells proceeds by this culture.

The progress of the differentiation induction into mesendoderm cells can also be evaluated by observing gene expression by RT-PCR in addition to by morphological observation. As the differentiation of pluripotent stem cells into mesendoderm cells proceeds, the expression of marker genes for stem cells, OCT4, NANOG, SOX2, ECAD and the like decreases while the expression of marker genes for mesendoderm cells, BRA, FGF4, WNT3, NCAD and the like is promoted.

The second culture medium used at the step (A1-2) may be similar to the above except that it is low in blood serum. That is, the second culture medium may contain a growth factor belonging to the TGF-β superfamily, and in addition, may contain a growth factor belonging to the Wnt family. The concentration of blood serum is preferably 0.05 to 2% (v/v), more preferably 0.05 to 1% (v/v), and even more preferably 0.1 to 0.5% (v/v).

The culture period at the step (A1-2) is, for example, 1 to 3 days, and preferably 1 to 2 days. The differentiation of mesendoderm cells into embryonic endoderm cells proceeds by this culture.

As described above, the progress of the differentiation induction into mesendoderm cells can also be evaluated by observing gene expression by RT-PCR in addition to by morphological observation.

Note that before proceeding to the following step (B1), the cells obtained may be concentrated, isolated and/or purified by a conventionally known method.
(Step (B1))

At the step (B1), the cells obtained at the step (A1) are cultured in the presence of FGF.

Examples of FGF include FGF-1, FGF-2 (bFGF), FGF-3, FGF-4, FGF-5, FGF-6, FGF-7, FGF-8, FGF-9, FGF-10, FGF-11, FGF-12, FGF-13, FGF-14, FGF-15, FGF-16, FGF-17, FGF-18, FGF-19, FGF-20, FGF-21, FGF-22, FGF-23 and the like. FGF-2 (bFGF), FGF-5, FGF-7, FGF-10 are preferred.

The concentration of FGF is preferably 5 to 150 ng/mL, more preferably 10 to 100 ng/mL, and even more preferably 20 to 80 ng/mL.

Further, a hedgehog pathway inhibitor is preferably added to a culture medium at the step (B1). The differentiation efficiency can be increased by adding a hedgehog pathway inhibitor along with FGF.

Hedgehog pathway inhibitors include KAAD-cyclopamine (28-[2-[[6-[(3-phenylpropanoyl)amino]hexanoyl]amino]ethyl]-17β,23β-epoxyveratraman-3-one), an analog of KAAD-cyclopamine, jervine (17,23β-epoxy-3β-hydroxyveratraman-11-one), an analog of jervine, a hedgehog pathway-blocking antibody and the like. Among these, KAAD-cyclopamine is preferred.

The concentration of a hedgehog pathway inhibitor is preferably 0.01 to 5 μM, more preferably 0.02 to 2 μM, and even more preferably 0.1 to 0.5 μM.

A container used for culture may be similar to that used at the step (A1). A culture medium may be similar to that used at the step (A1) except for the factors described above and the concentration of blood serum in the culture medium. The concentration of blood serum in a culture medium is preferably 0.1 to 5% (v/v), more preferably 0.5 to 5% (v/v), and even more preferably 1 to 5% (v/v).

Note that a culture medium with a concentration of blood serum higher than that at the step (A1) is preferably used at the step (B1) when a low-serum culture medium is used at the step (A1).

According to a preferred embodiment, used is a low-serum RPMI1640 culture medium with added FGF-10, KAAD-cyclopamine, an antibiotic such as penicillin and streptomycin, L-glutamine, or a dipeptide comprising L-glutamine.

The culture period at the step (B1) is, for example, 1 to 6 days, and preferably 2 to 4 days.

The progress of the differentiation induction can be evaluated by observing gene expression by RT-PCR in addition to by morphological observation. As differentiation proceeds, the gene expression of HNF1B, HNF4A and the like is promoted.

Note that before proceeding to the following step (C1), the cells obtained may be concentrated, isolated and/or purified by a conventionally known method.
(Step (C1))

At the step (C1), the cells obtained at the step (B1) are cultured in the presence of retinoid.

Examples of retinoid include retinol, retinal, retinoic acid and the like. Among these, retinoic acid is preferred.

The concentration of retinoid is preferably 0.2 to 10 μM, more preferably 0.4 to 8 μM, and even more preferably 1 to 4 μM.

Further, a hedgehog pathway inhibitor is preferably added to a culture medium at the step (C1). The differentiation efficiency can be increased by adding a hedgehog pathway inhibitor along with retinoid.

Hedgehog pathway inhibitors include KAAD-cyclopamine, an analog of KAAD-cyclopamine, jervine, an analog of jervine, a hedgehog pathway-blocking antibody and the like. Among these, KAAD-cyclopamine is preferred.

The concentration of a hedgehog pathway inhibitor is preferably 0.01 to 5 μM, more preferably 0.02 to 2 μM, and even more preferably 0.1 to 0.5 μM.

Further, FGF is preferably added to a culture medium at the step (C1). The differentiation efficiency can be increased by adding FGF along with retinoid.

Examples of FGF include FGF-1, FGF-2 (bFGF), FGF-3, FGF-4, FGF-5, FGF-6, FGF-7, FGF-8, FGF-9, FGF-10, FGF-11, FGF-12, FGF-13, FGF-14, FGF-15, FGF-16, FGF-17, FGF-18, FGF-19, FGF-20, FGF-21, FGF-22, FGF-23 and the like. FGF-2 (bFGF), FGF-5, FGF-7, FGF-10 are preferred.

The concentration of FGF is preferably 0.5 to 50 ng/mL, more preferably 1 to 25 ng/mL, and even more preferably 2 to 10 ng/mL.

Further, a growth factor belonging to the TGF-β superfamily may be added to a culture medium at the step (C1).

The concentration of a growth factor belonging to the TGF-β superfamily is preferably 5 to 250 ng/mL, more preferably 10 to 200 ng/mL, and even more preferably 20 to 150 ng/mL.

A container used for culture may be similar to that used at the step (B1). A culture medium may basically be similar to that used at the step (B1) except for the factors described above. However, a blood serum substitute is preferably added to a culture medium instead of blood serum. For commercially available products of blood serum substitutes, a B-27TM supplement, an N-2 supplement, a Knockout™ blood serum substitute from Invitrogen and the like are available. Among these, a B-27TM supplement is preferred.

The concentration of a B-27TM supplement is preferably 0.1 to 10% (v/v), more preferably 0.2 to 5% (v/v), and even more preferably 0.4 to 2.5% (v/v). Note that since the above B-27TM supplement is sold as a 50× stock solution, the B-27TM supplement may be added to a culture medium in 5× to 500× dilution in order to give a concentration of the B-27TM supplement of 0.1 to 10% (v/v).

According to a preferred embodiment, used is a serum-free DMEM/ham F12 medium with added retinoic acid, KAAD-cyclopamine, FGF-10, an antibiotic such as penicillin and streptomycin, a B-27TM supplement.

The culture period at the step (C1) is, for example, 1 to 6 days, and preferably 2 to 4 days.

The progress of differentiation induction can also be evaluated by confirming gene expression by RT-PCR in addition to by morphological observation. As differentiation proceeds, the gene expression of PDX1, HNF6, HLXB9 and the like is promoted.

Note that before proceeding to the following step (D1), the cells obtained may be concentrated, isolated and/or purified by a known method.

(Step (D1))

At the step (D1), the cells obtained at the step (C1) are cultured in the presence of a γ-secretase inhibitor.

γ-secretase inhibitors include DAPT (N—[N-(3,5-difluorophenacetyl-L-alanyl)]-S-phenylglycine-tert-butyl ester), L-685458 ([1S-benzyl-4R-[1-(1S-carbamoyl-2-phenethylcarbamoyl)-1S-3-methylbutylcarbamoyl]-2R-hydroxy-5-phenethylpentyl]carbamic acid tert-butyl ester) and the like. Among these, DAPT is preferred.

The concentration of a γ-secretase inhibitor is preferably 1 to 50 µM, more preferably 2 to 40 µM, and even more preferably 5 to 20 µM.

Further, exendin-4 is preferably added to a culture medium at the step (D1). The differentiation efficiency can be increased by adding exendin-4 along with a γ-secretase inhibitor.

The concentration of exendin-4 is preferably 5 to 150 ng/mL, more preferably 10 to 100 ng/mL, and even more preferably 20 to 80 ng/mL.

A container and culture medium used for culture may be similar to those used at the step (C1). That is, a blood serum substitute is preferably added to a culture medium.

According to a preferred embodiment, used is a serum-free DMEM/ham F12 medium with added DAPT, exendin-4, an antibiotic such as penicillin and streptomycin, a B-27TM supplement.

The culture period at the step (D1) is, for example, 1 to 6 days, and preferably 2 to 3 days.

The progress of differentiation induction can also be evaluated by observing gene expression by RT-PCR in addition to by morphological observation. The gene expression of NKX6-1, NGN3, PAX4, NKX2-2 and the like is promoted as differentiation proceeds.

Note that before proceeding to the following step (E1), the cells obtained may be concentrated, isolated and/or purified by a conventionally known method.

(Step (E1))

At the step (E1), the cells obtained at the step (D1) are cultured in the presence of at least one factor selected from the group consisting of exendin-4, HGF, IGF-1 and nicotinamide.

Preferably two or more, more preferably 3 or more of exendin-4, HGF, IGF-1 and nicotinamide are added.

The concentration of exendin-4 is preferably 5 to 150 nM, more preferably 10 to 100 nM, and even more preferably 20 to 80 nM.

The concentration of HGF is preferably 5 to 150 ng/mL, more preferably 10 to 100 ng/mL, and even more preferably 20 to 80 ng/mL.

The concentration of IGF-1 is preferably 5 to 150 ng/mL, more preferably 10 to 100 ng/mL, and even more preferably 20 to 80 ng/mL.

The concentration of nicotinamide is preferably 1 to 30 mM, more preferably 3 to 20 mM, and even more preferably 5 to 15 mM.

A container and culture medium used for culture may be similar to those used at the step (D1). That is, a blood serum substitute is preferably added to a culture medium.

According to a preferred embodiment, used is a serum-free CMRL1066 culture medium with added exendin-4, HGF, IGF-1, an antibiotic such as penicillin, streptomycin, a B-27TM supplement.

The culture period at the step (E1) is, for example, 3 to 20 days, and preferably 3 to 10 days.

Pancreatic hormone-producing cells are obtained with this step (E1).

The progress of differentiation induction into pancreatic hormone-producing cells can be evaluated by observing gene expression by RT-PCR in addition to detecting the production of a pancreatic hormone such as insulin, glucagon, somatostatin and the like. The expression of at least one gene of INS, GCG, GHRL, SST, PPY and the like is promoted as differentiation proceeds.

[Second Differentiation Induction Method]

A second differentiation induction method is in accordance with a method described in Nonpatent Document 4. This reference is incorporated herein by reference.

The second differentiation induction method comprises the following steps (A2) to (D2). The peptide according to the above (d) or (e) is added to a culture medium in at least one of these steps. Note that when adding a differentiation-induction promoting agent at a certain step, it may be added at the beginning of the step or may be added at the middle of the step. Although the peptide according to the above (d) or (e) may be added in at least one of the steps (C2) to (D2), the peptide according to the above (d) or (e) is preferably added in all of the steps (A2) to (D2).
- (A2) A step of culturing pluripotent stem cells in the presence of at least one factor selected from the group consisting of growth factors belonging to the TGF-β superfamily, growth factors belonging to the Wnt family and GSK-3 (glycogen synthase kinase 3) inhibitors.
- (B-2) A step of culturing cells obtained at the above step (A2) in the presence of a growth factor belonging to the TGF-β superfamily.
- (C2) A step of culturing cells obtained at the above step (B2) in the presence of retinoid.
- (D2) A step of culturing cells obtained at the above step (C2) in the presence of at least one factor selected from the group consisting of cAMP (cyclic adenosine monophosphate) increasing agents, dexamethasone, TGF-β1 type receptor inhibitors and nicotinamide.

(Step (A2))

At the step (A2), pluripotent stem cells are cultured in the presence of at least one factor selected from the group consisting of growth factors belonging to the TGF-β superfamily, growth factors belonging to the Wnt family and GSK-3 inhibitors.

Growth factors belonging to the TGF-β superfamily include activin, nodal, BMP and the like. Among these, activin is preferred. Examples of activin include activin A, activin B, activin AB and the like. Among these, activin A is preferred.

The concentration of a growth factor belonging to the TGF-β superfamily is preferably 5 to 250 ng/mL, more preferably 10 to 200 ng/mL, and even more preferably 50 to 150 ng/mL.

Growth factors belonging to the Wnt family include Wnt1, Wnt3a, Wnt5a, Wnt7a and the like. Wnt1, Wnt3a are preferred, and Wnt3a is more preferred.

The concentration of a growth factor belonging to the Wnt family is preferably 1 to 1000 ng/mL, more preferably 10 to 100 ng/mL, and even more preferably 10 to 50 ng/mL.

Either a GSK-3α inhibitor or a GSK-3β inhibitor may be used as a GSK-3 inhibitor, but a GSK-3β inhibitor is preferably used. Specific examples include CHIR99021 (6-[[2-[[4-(2,4-dichlorophenyl)-5-(5-methyl-1H-imidazole-2-yl)-2-pyrimidinyl]amino]ethyl]amino]-3-pyridinecarbonitrile), SB415286 (3-[(3-chloro-4-hydroxyphenyl)amino]-4-(2-nitrophenyl)-1H-pyrrole-2,5-dione), SB216763 (3-(2,4-dichlorophenyl)-4-(1-methyl-1H-indole-3-yl)-1H-pyrrole-2,5-dione), indirubin-3'-monoxime(3-[(3E)-3-(hydroxyimino)-2,3-dihydro-1H-indole-2-ylidene]-2,3-dihydro-1H-indole-2-one), kenpaullone (7,8-dihydro-9-bromoindolo[3,2-d][1]benzoazepin-6(5H)-one) and the like. Among these, CHIR99021 is preferably used.

The concentration of a GSK-3 inhibitor is preferably 0.01 to 20 µM, more preferably 0.1 to 20 µM, and even more preferably 1 to 5 µM.

Further, at the step (A2), an additional factor which can increase a differentiation efficiency may be added to a culture medium. Additional factors include, for example, PDGF, EGF, VEGF, KGF, HGF, NGF, GDF, GLP, nicotinamide, exendin-4, retinoic acid, ethanolamine, parathyroid hormone, progesterone, aprotinin, hydrocortisone, gastrin, steroid alkaloid, copper chelators (triethylenepentamine and the like), forskolin, sodium butyrate, noggin, valproic acid, trichostatin A, Indian hedgehog, Sonic hedgehog, proteasome inhibitors, notch pathway inhibitors, hedgehog pathway inhibitors and the like.

As a container used for culture, preferred is a culture plate coated with a scaffold of a biocompatible material in view of a differentiation induction capability, a functional expression capability, viability and the like. Scaffolds include laminin, fibronectin, collagen, heparan sulphate proteoglycan, gelatin, entactin, polyornithine and the like. MATRIGEL™, a growth factor-reduced MATRIGEL™ from Becton Dickinson and the like are available as commercial products. In particular, a culture plate coated with MATRIGEL™ is preferably used.

A culture medium used for culture may be prepared by adding various nutrient sources and other components required for cell maintenance and proliferation to a basal medium which can be used for culturing animal cells.

Basal media include RPMI1640 culture medium, DMEM culture medium, CMRL1066 culture medium, Ham F12 culture medium, Eagle MEM culture medium, Glasgow MEM culture medium, IMEM Zinc Option culture medium, IMDM culture medium, William E culture medium, Fischer culture medium, McCoy culture medium, BME culture medium, α-MEM culture medium, BGJb culture medium, Medium 199 culture medium, or mixed media thereof and the like.

Nutrient sources include carbon sources such as glycerol, glucose, fructose, sucrose, lactose, starch, dextrin; hydrocarbons such as fatty acid, fats and oils, lecithin, alcohol; nitrogen sources such as ammonium sulfate, ammonium nitrate, ammonium chloride, urea, sodium nitrate; inorganic salts such as sodium salts, potassium salts, magnesium salts, calcium salts, phosphate salts; various vitamins; various amino acids; and the like.

Other components include antibiotics such as penicillin, streptomycin; cholera toxin; insulin; transferrin; selenious acid; albumin; 2-mercaptoethanol; blood serum or blood serum substitutes; and the like. For insulin, transferrin and selenious acid, ITS-X, ITS-A, ITS-G from Invitrogen and the like are available as commercial products. Further, for blood serum substitutes, a B-27™ supplement, an N-2 supplement, a Knockout™ blood serum substitute from Invitrogen and the like are available as commercial products.

Here, it is known that sufficiently low contents of insulin, IGF and the like in a culture medium are important in order to increase the differentiation efficiency at the step (A2). Therefore, a serum-free culture medium or a low-serum culture medium is preferably used at the step (A2). The serum concentration is preferably 0 to 3% (v/v), and more preferably 0 to 2% (v/v).

According to a preferred embodiment, used is a low-serum RPMI1640 culture medium with added activin A, CHIR99021.

The culture period at the step (A2) is, for example, 1 to 3 days, and preferably 1 to 2 days.

(Step (B2))

At the step (B2), cells obtained at the step (A2) are cultured in the presence of a growth factor belonging to the TGF-β superfamily.

Growth factors belonging to the TGF-β superfamily include activin, nodal, BMP and the like. Among these, activin is preferred. Examples of activin include activin A, activin B, activin AB and the like. Among these, activin A is preferred.

The concentration of a growth factor belonging to the TGF-β superfamily is preferably 5 to 250 ng/mL, more preferably 10 to 200 ng/mL, and even more preferably 50 to 150 ng/mL.

A container and culture medium used for culture may be similar to those used at the step (A2). That is, according to a preferred embodiment, used is a low-serum RPMI1640 culture medium with added activin A.

The culture period at the step (B2) is, for example, 1 to 4 days, and preferably 1 to 3 days.

(Step (C2))

At the step (C2), the cells obtained at the step (B2) are cultured in the presence of retinoid.

Examples of retinoid include retinol, retinal, retinoic acid and the like. Among these, retinoic acid is preferred.

The concentration of retinoid is preferably 0.2 to 10 µM, more preferably 0.4 to 8 µM, and even more preferably 1 to 4 µM.

Further, a BMP receptor inhibitor is preferably added to a culture medium at the step (C2).

BMP receptor inhibitors include dorsomorphin (6-[4-[2-(1-piperidinyl)ethoxy]phenyl]-3-(4-pyridyl)pyrazolo[1,5-a]pyrimidine), LDN-193189 (4-(6-(4-piperazine-1-yl)phenyl)pyrazolo[1,5-a]pyrimidine-3-yl)quinoline) and the like. Among these, dorsomorphin is preferred.

The concentration of a BMP receptor inhibitor is preferably 0.2 to 5 µM, more preferably 0.3 to 3 µM, and even more preferably 0.5 to 2 µM.

Further, a TGF-β1 type receptor inhibitor is preferably added to a culture medium at the step (C2).

TGF-β1 type receptor inhibitors include SB431542 (4-[4-(1,3-benzodioxole-5-yl)-5-(2-pyridinyl)-1H-imidazole-2-yl]benzamide), SB525334 (6-[2-(1,1-dimethylethyl)-5-(6-methyl-1,2-pyridinyl)-1H-imidazole-4-yl]quinoxaline), LY364947 (4-[3-(2-pyridinyl)-1H-pyrazol-4-yl]quinoline) and the like. Among these, SB431542 is preferred. Further, Alk5 inhibitor II from Calbiochem may be used as a TGF-β1 type receptor inhibitor.

The concentration of a TGF-β1 type receptor inhibitor is preferably 1 to 50 µM, more preferably 2 to 30 µM, and even more preferably 5 to 20 µM.

A container used for culture may be similar to that used at the step (B2). A culture medium may basically be similar to that used at the step (B2) except for the factors described above. However, a blood serum substitute is preferably added to a culture medium instead of blood serum. A B-27TM supplement, an N-2 supplement, a Knockout™ blood serum substitute from Invitrogen and the like are available as commercial products of blood serum substitutes. Among these, a B-27TM supplement is preferred.

The concentration of a B-27TM supplement is preferably 0.1 to 10% (v/v), more preferably 0.2 to 5% (v/v), and even more preferably 0.4 to 2.5% (v/v). Note that since the above B-27TM supplement is sold as a 50× stock solution, the B-27TM supplement is added to a culture medium in 5× to 500× dilution in order to give a concentration of the B-27TM supplement of 0.1 to 10% (v/v).

According to a preferred embodiment, used is a serum-free IMEM Zinc Option culture medium with added retinoic acid, dorsomorphin, SB431542, a B-27TM supplement.

The culture period at the step (C2) is, for example, 5 to 9 days, and preferably 6 to 8 days.

(Step (D2))

At the step (D2), the cells obtained at the step (C2) are cultured in the presence of at least one factor selected from the group consisting of cAMP increasing agents, dexamethasone, TGF-β1 type receptor inhibitors and nicotinamide.

Preferably two or more, more preferably 3 or more of cAMP increasing agents, dexamethasone, TGF-β1 type receptor inhibitors and nicotinamide are added.

cAMP increasing agents include adenylate cyclase activating agents such as forskolin; phosphodiesterase inhibitors such as 3-isobutyl-1-methylxanthin; cAMP analogs such as dibutyryl cAMP; and the like. Among these, forskolin is preferred.

The concentration of a cAMP increasing agent is preferably 1 to 50 µM, more preferably 2 to 30 µM, and even more preferably 5 to 20 µM.

The concentration of dexamethasone is preferably 1 to 50 µM, more preferably 2 to 30 µM, and even more preferably 5 to 20 µM.

TGF-β1 type receptor inhibitors include SB431542, SB525334, LY364947 and the like. Among these, SB431542 is preferred. Further, Alk5 inhibitor II from Calbiochem may also be used as a TGF-β1 type receptor inhibitor.

The concentration of a TGF-β1 type receptor inhibitor is preferably 1 to 50 µM, more preferably 2 to 30 µM, and even more preferably 5 to 20 µM.

The concentration of nicotinamide is preferably 1 to 30 mM, more preferably 3 to 20 mM, and even more preferably 5 to 15 mM.

A container and culture medium used for culture may be similar to those used at the step (C2). That is, a blood serum substitute is preferably added to a culture medium.

According to a preferred embodiment, used is a serum-free IMEM Zinc Option culture medium with added forskolin, dexamethasone, Alk5 inhibitor II, nicotinamide, a B-27TM supplement.

The culture period at the step (D2) is, for example, 9 to 13 days, and preferably 10 to 12 days.

Pancreatic hormone-producing cells are obtained at this step (D2).

The progress of differentiation induction into pancreatic hormone-producing cells can be evaluated by confirming gene expression by RT-PCR in addition to confirming the production of a pancreatic hormone such as insulin, glucagon, somatostatin and the like. At least one gene expression of marker genes for pancreatic hormone-producing cells: INS, GCG, GHRL, SST, PPY and the like is promoted as the differentiation of pluripotent stem cells into pancreatic hormone-producing cells proceeds.

Differentiation Induction of Pancreas Tissue Stem/Precursor Cells into Pancreatic Hormone-Producing Cells In order to induce the differentiation of pancreas tissue stem/precursor cells into pancreatic hormone-producing cells, the peptide according to the above (d) or (e) may be added to a culture medium in the course of the differentiation-inducing process. There is no limitation for a method of inducing the differentiation of pancreas tissue stem/precursor cells into pancreatic hormone-producing cells, and any conventionally known method can be used. The concentration of the peptide according to the above (d) or (e) in a culture medium is preferably 10 to 200 ng/mL, more preferably 50 to 150 ng/mL, and even more preferably 60 to 120 ng/mL.

Below, an example of a method of inducing the differentiation of pancreas tissue stem/precursor cells into pancreatic hormone-producing cells will be described, but it is not limited to this example.

The differentiation induction method described below is in accordance with a method described in Nonpatent Document 2. This reference is incorporated herein by reference.

This differentiation induction method comprises the following steps (A3) to (E3). The peptide according to the above (d) or (e) is added to a culture medium in at least one of these steps. Note that when adding a differentiation-induction promoting agent at a certain step, it may be added at the beginning of the step or may be added at the middle of the step. Although the peptide according to the above (d) or (e) may be added in at least one of the steps (D3) to (E3), the peptide according to the above (d) or (e) is preferably added in all of the steps (A3) to (E3).

(A3) A step of culturing pancreas tissue stem/precursor cells in the absence of a growth factor belonging to the TGF-β superfamily, retinoid, FGF and nicotinamide (B3) A step of culturing cells obtained at the above step (A3) in the presence of a growth factor belonging to the TGF-β superfamily.

(C3) A step of culturing cells obtained at the above step (B3) in the presence of retinoid.

(D3) A step of culturing cells obtained at the above step (C3) in the presence of FGF.

(E3) A step of culturing cells obtained at the above step (D3) in the presence of nicotinamide.

(Step (A3))

At the step (A3), pancreas tissue stem/precursor cells are cultured in the absence of a growth factor belonging to the TGF-β superfamily, retinoid, FGF and nicotinamide.

For a container used for the culture, preferred is a culture plate coated with a scaffold of a biocompatible material in view of a differentiation induction capability, a functional expression capability, viability and the like. Scaffolds include laminin, fibronectin, collagen, heparan sulphate proteoglycan, gelatin, entactin, polyornithine and the like. MATRIGEL™, a growth factor-reduced MATRIGEL™ from Becton Dickinson and the like are available as commercial products. In particular, a culture plate coated with MATRIGEL™ is preferably used.

A culture medium used for culture may be prepared by adding various nutrient sources and other components required for cell maintenance and proliferation to a basal medium which can be used for culturing animal cells.

Basal media include RPMI1640 culture medium, DMEM culture medium, CMRL1066 culture medium, Ham F12 culture medium, Eagle MEM culture medium, Glasgow MEM culture medium, IMEM Zinc Option culture medium, IMDM culture medium, William E culture medium, Fischer culture medium, McCoy culture medium, BME culture medium, α-MEM culture medium, BGJb culture medium, Medium 199 culture medium, or mixed media thereof and the like.

Nutrient sources include carbon sources such as glycerol, glucose, fructose, sucrose, lactose, starch, dextrin; hydrocarbons such as fatty acid, fats and oils, lecithin, alcohol; nitrogen sources such as ammonium sulfate, ammonium nitrate, ammonium chloride, urea, sodium nitrate; inorganic salts such as sodium salts, potassium salts, magnesium salts, calcium salts, phosphate salts; various vitamins; various amino acids; and the like.

Other components include antibiotics such as penicillin, streptomycin; cholera toxin; insulin; transferrin; selenious acid; 2-mercaptoethanol; albumin; blood serum or blood serum substitutes; and the like. For insulin, transferrin and selenious acid, ITS-X, ITS-A, ITS-G from Invitrogen and the like are available as commercial products. Further, for blood serum substitutes, a B-27™ supplement, an N-2 supplement, a Knockout™ blood serum substitute from Invitrogen and the like are available as commercial products.

According to a preferred embodiment, used is a serum-free DMEM/ham F12 with added an antibiotic such as penicillin, streptomycin, insulin, transferrin, selenious acid, 2-mercaptoethanol, albumin.

The concentration of insulin is preferably 2 to 30 μg/mL, more preferably 5 to 20 μg/mL. The concentration of transferrin is preferably 1 to 20 μg/mL, more preferably 3 to 10 μg/mL. The concentration of selenious acid is preferably 1 to 20 ng/mL, more preferably 5 to 20 ng/mL. The concentration of 2-mercaptoethanol is preferably 50 to 200 μM, more preferably 50 to 100 μM. The concentration of albumin is preferably 1 to 10 ng/mL, more preferably 2 to 5 ng/mL.

The culture period at the step (A3) is, for example, 1 to 3 days, and preferably 1 to 2 days.

(Step (B3))

At the step (B3), the cells obtained at the step (A3) are cultured in the presence of a growth factor belonging to the TGF-β superfamily.

Growth factors belonging to the TGF-β superfamily include activin, nodal, BMP and the like. Among these, activin is preferred. Examples of activin include activin A, activin B, activin AB and the like. Among these, activin A is preferred.

The concentration of a growth factor belonging to the TGF-β superfamily is preferably 5 to 250 ng/mL, more preferably 10 to 200 ng/mL, and even more preferably 50 to 150 ng/mL.

A container used for culture may be similar to that used at the step (A3). A culture medium may be similar to that used at the step (A3) except that a growth factor belonging to the TGF-β superfamily is added. That is, according to a preferred embodiment, used is a serum-free DMEM/ham F12 with added an antibiotic such as penicillin, streptomycin, insulin, transferrin, selenious acid, 2-mercaptoethanol, albumin.

The culture period at the step (B3) is, for example, 2 to 6 days, and preferably 3 to 5 days.

(Step (C3))

At the step (C3), the cells obtained at the step (B3) are cultured in the presence of retinoid.

Examples of retinoid include retinol, retinal, retinoic acid and the like. Among these, all-trans retinoic acid is preferred.

The concentration of retinoid is preferably 0.2 to 10 μM, more preferably 0.4 to 8 μM, and even more preferably 1 to 4 μM.

A container used for culture may be similar to that used at the step (A3). A culture medium may be similar to that used at the step (A3) except that a growth factor belonging to the TGF-β superfamily is added.

According to a preferred embodiment, used is a serum-free DMEM/ham F12 with added all-trans retinoic acid, an antibiotic such as penicillin, streptomycin, insulin, transferrin, selenious acid, 2-mercaptoethanol, albumin.

The culture period at the step (C3) is, for example, 2 to 6 days, and preferably 3 to 5 days.

(Step (D3))

At the step (D3), the cells obtained at the step (C3) are cultured in the presence of FGF.

Examples of FGF include FGF-1, FGF-2 (bFGF), FGF-3, FGF-4, FGF-5, FGF-6, FGF-7, FGF-8, FGF-9, FGF-10, FGF-11, FGF-12, FGF-13, FGF-14, FGF-15, FGF-16, FGF-17, FGF-18, FGF-19, FGF-20, FGF-21, FGF-22, FGF-23 and the like. FGF-2 (bFGF), FGF-5, FGF-7, FGF-10 are preferred.

The concentration of FGF is preferably 1 to 30 ng/mL, more preferably 2 to 20 ng/mL, and even more preferably 5 to 15 ng/mL.

A container used for culture may be similar to that used at the step (A3). A culture medium may basically be similar to that used at the step (C3) except that FGF is added.

According to a preferred embodiment, used is a serum-free DMEM/ham F12 with added FGF-2 (bFGF), an antibiotic such as penicillin, streptomycin, insulin, transferrin, selenious acid, albumin.

The culture period at the step (D3) is, for example, 1 to 5 days, and preferably 2 to 4 days.

(Step (E3))

At the step (E3), the cells obtained at the step (D3) are cultured in the presence of nicotinamide.

The concentration of nicotinamide is preferably 1 to 30 mM, more preferably 3 to 20 mM, and even more preferably 5 to 15 mM.

Further, FGF is preferably added to a culture medium at the step (E3).

Examples of FGF include FGF-1, FGF-2 (bFGF), FGF-3, FGF-4, FGF-5, FGF-6, FGF-7, FGF-8, FGF-9, FGF-10, FGF-11, FGF-12, FGF-13, FGF-14, FGF-15, FGF-16, FGF-17, FGF-18, FGF-19, FGF-20, FGF-21, FGF-22, FGF-23 and the like. FGF-2 (bFGF), FGF-5, FGF-7, FGF-10 are preferred.

The concentration of FGF is preferably 1 to 30 ng/mL, more preferably 2 to 20 ng/mL, and even more preferably 5 to 15 ng/mL.

A container used for the culture may be similar to that used at the step (A3). A culture medium may basically be similar to that used at the step (D3) except that nicotinamide is added.

According to a preferred embodiment, used is a serum-free DMEM/ham F12 with added nicotinamide, FGF-2 (bFGF), an antibiotic such as penicillin, streptomycin, insulin, transferrin, selenious acid, albumin.

The culture period at the step (E3) is, for example, 3 to 20 days, and preferably 3 to 10 days.

Pancreatic hormone-producing cells are obtained at this step (E3).

The progress of differentiation induction into pancreatic hormone-producing cells can be evaluated by confirming gene expression by RT-PCR in addition to confirming the production of a pancreatic hormone such as insulin, glucagon, somatostatin and the like. At least one gene expression of marker genes for pancreatic hormone-producing cells: INS, GCG, GHRL, SST, PPY and the like is promoted as the differentiation of pancreas tissue stem/precursor cells into pancreatic hormone-producing cells proceeds.

Method of Forming a Cluster of Pancreatic Hormone-Producing Cells for Regenerative Medicine The method of forming a cluster of pancreatic hormone-producing cells for regenerative medicine according to the present invention include the proliferation method according to the present invention and/or the differentiation-formation method according to the present invention.

As described above, the differentiation-formation method according to the present invention can efficiently induce the differentiation of pluripotent stem cells or pancreas tissue stem/precursor cells into pancreatic hormone-producing cells. Further, the proliferation method according to the present invention can promote the growth of pancreatic hormone-producing cells. Therefore, a cluster of pancreatic hormone-producing cells suitable for regenerative medicine can be formed by using these alone or in combination. The above cluster of pancreatic hormone-producing cells may be a mass of pancreatic islet-like cells, or may be a sheet of pancreatic islet-like cells. Further, the cluster of pancreatic hormone-producing cells preferably comprises α cells or β cells.

EXAMPLES

Below, the present invention will be described in detail with reference to Examples, but the present invention shall not be construed as limited to the following description.

Example 1: Growth Promotion of Pancreatic β Cells (1)

MIN6 cells provided by Dr. Miyazaki at Osaka University were used as a pancreatic β cell line. MIN6 cells were maintained in a DMEM culture medium with added 15% (v/v) of FBS.

First, MIN6 cells were plated on a collagen-coated 8-well slide chamber (BD Falcon, Product Number 354630) at a cell density of 1×104 cells/well. After 24 hours, the culture medium was replaced with a DMEM culture medium with added 0.5% (v/v) of FBS, and then serum starvation was performed for 72 hours. Note that the culture medium was replaced with a fresh culture medium 48 hours after the start of serum starvation. Subsequently, at 72 hours after the start of serum starvation, a chemically synthesized peptide (betagenin) consisting of the amino acid sequence set forth in SEQ ID NO: 1 was added to the culture medium so that the final concentration was 0.3 nM or 1 nM. As a control, dimethyl sulfoxide (DMSO), which was a vehicle for betagenin, was added at an equivalent addition amount.

At 24 hours after adding betagenin or DMSO, 5-ethynyl-2'-deoxyuridine (EdU) was added so that the final concentration was 10 µM, and then cultured for 2 hours. Then, cell proliferation assay was performed using a Click-iT™ Edu Alexa Flour™ 594 Imaging Kit in accordance with the accompanying instruction (Invitrogen, Product Number C10339).

EdU taken up into cells was visualized as red fluorescence using Alexa Flour™ 594, and observed with a fluorescence microscope (Carl Zeiss). FIG. 1 shows relative EdU fluorescence intensities when the fluorescence intensity of control is taken as 1.0.

As shown in FIG. 1, the relative EdU fluorescence intensity showed 2.7 to 2.8 times increase by adding betagenin peptide.

The results show that the growth of MIN6 cells is promoted by adding betagenin peptide to the culture medium.

Example 2: Differentiation Induction of Human iPS Cells into Pancreatic Hormone-Producing Cells (1)

As human iPS cells, used were 253G1 cells purchased from the cell bank at RIKEN, TIG3/KOSM cells provided by Dr. Mitani at Saitama Medical University, 200-9 cells, a clone in which a reporter gene is introduced into TIG3/KOSM cells. TIG3/KOSM cells were established at The National Institute of Advanced Industrial Science and Technology by introducing 4 factors (the OCT gene, the KLF gene, the SOX gene, the MYC gene) into TIG-3 cells using Sendai virus (Nishimura, K. et al., J. Biol. Chem., 286, pp. 4760-4771 (2011)).

These cells were cultured/maintained in an ES cell culture medium (DMEM/ham F12, 20% KSR, nonessential amino acid, 2 mM L-glutamine, 0.1 mM 2-mercaptoethanol, 5.2 mM NaOH) with added 4 ng/mL FGF-2 (Global Stem) and penicillin/streptomycin (Nacalai Tesque, Inc.) along with SNL76/7 cells (DS Pharma Biomedical) treated with mitomycin-C. CTK (0.25% trypsin, 1 mg/mL collagenase IV, 20% KSR, 1 mM CaCl2 in PBS) was used for cell detachment, and diluted at a ratio of 1:3 to 1:4 to perform passage culture.

Cells were detached with trypsin-EDTA 3 days before the start of differentiation induction, and plated at a cell density of 6.3×104 cells/cm2, and cultured for 1 day in an ES cell culture medium with added 10 µM Y-27632 (Wako), 4 ng/mL FGF-2 and penicillin/streptomycin along with STO cells treated with mitomycin-C. Subsequently, they were further cultured for 2 days in an ES cell culture medium with added 4 ng/mL FGF-2 and penicillin/streptomycin.

On the first day of the start of differentiation induction, the culture medium was replaced with a RPMI1640 culture medium (Nacalai Tesque, Inc.) with added 2% (v/v) FBS, 100 ng/mL activin A (SBI) and 3 µM CHIR99021 (Axon Medchem), and cultured for 1 day (Step (A2)).

Subsequently, the culture medium was replaced with a RPMI1640 culture medium with added 2% (v/v) FBS and 100 ng/mL activin A, and cultured for 2 days (Step (B2)).

Then, the culture medium was replaced with an IMEM Zinc Option culture medium (Gibco) with added 1% (v/v) B-27TM supplement (Invitrogen), 1 µM dorsomorphin (Calbiochem), 2 µM retinoic acid (Sigma) and 10 µM SB431542 (Sigma), and cultured for 7 days (Step (C2)).

Finally, the culture medium was replaced with an IMEM Zinc Option culture medium with added 1% (v/v) B-27TM supplement, 10 mM forskolin (Wako), 10 µM dexamethasone (Wako), 5 µM Alk5 inhibitor II (Calbiochem), 10 µM nicotinamide (Wako) and 3 nM betagenin, and cultured for 11 days (Step (D2)). As a control, DMSO, which was a solvent for betagenin, was added at an equivalent addition amount.

(Quantitative RT-PCR Analysis)

The gene expression of insulin was confirmed by quantitative RT-PCR for the cells (n=2 for each of the betagenin addition group and the control group) obtained from 253G1 cells via the above steps (A2) to (D2). Specifically, total RNA was first extracted from the cells using a SV Total RNA Isolation System (Promega), and reverse transcription reactions were performed with BioScript™ transcriptase (Bioline), and then quantitative PCR analysis was performed using SYBR™ Green PCR Master Mix (Applied Biosystems). Primer sequences are shown below.

```
HsINS_31F:    GCCATCAAGCAGATCACTGT  (SEQ ID NO: 7)

HsINS_149R:   CAGGTGTTGGTTCACAAAGG  (SEQ ID NO: 8)
```

PCR products were separated by 3% agarose gel electrophoresis, and visualized with ethidium bromide, BioDoc-It Imaging System (BMbio).

Figure 2:
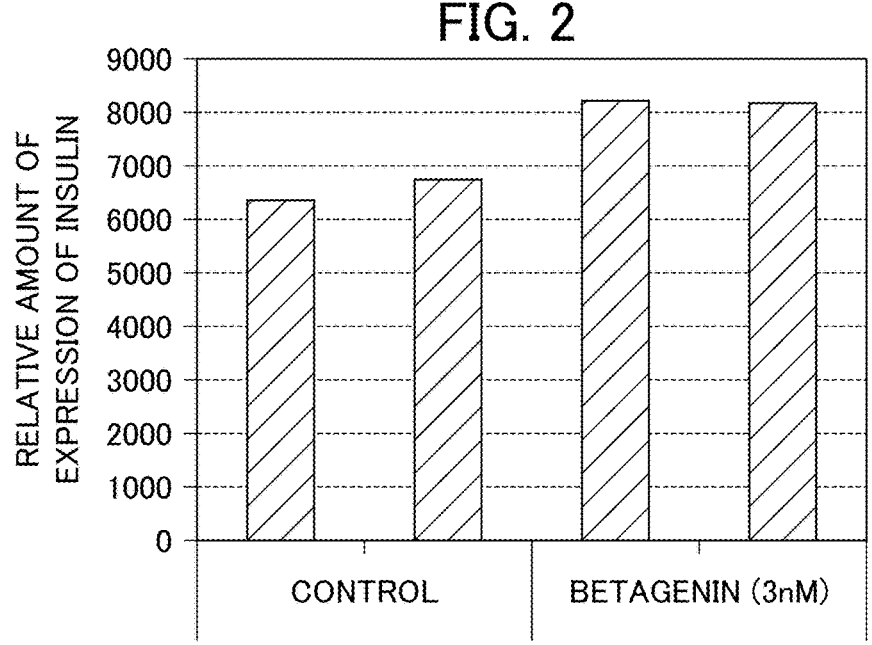
FIG. 2 shows relative expression amounts of insulin in cells obtained by differentiation induction when the peptide (betagenin) consisting of the amino acid sequence set forth in SEQ ID NO: 1 was added to a culture medium in the course of a differentiation induction process of human iPS cells (253G1 cells) into pancreatic hormone-producing cells.

FIG. 2 shows the amount of insulin expression in each of the cells obtained via the step (D2). FIG. 2 shows the relative amounts of expression when the amount of insulin expression in the cells on Day 10 of the start of differentiation induction is taken as 1.

As shown in FIG. 2, the amount of insulin expression was increased by adding betagenin.

The results show that the differentiation induction efficiency of human iPS cells into pancreatic hormone-producing cells can be improved by adding betagenin to a culture medium.

(Immunostaining)

The cells obtained from 200-9 cells, TIG3/KOSM cells or 253G1 cells via the above steps (A2) to (D2) were fixed with 4% paraformaldehyde for 5 minutes, and washed with PBS, and then further washed with 0.2% Triton-X/PBS for 15 minutes. After washed, blocking treatment was performed with 4% goat serum/PBS for 20 minutes. Rabbit anti C-peptide antibody (CST Japan) diluted 100 times with 1% BSA/PBS (antibody diluting solution) and guinea pig anti-insulin antibody (Dako) diluted 400 times with the antibody dilution solution were used as primary antibodies, and treated for 2 hours at 37° C. or overnight at 4° C. After treated with the primary antibodies, 5-minute wash with PBS was repeated for 3 times. Alexa Flour™ 488 and Alexa Flour™ 568 were diluted 200 to 500 times with the antibody diluting solution were used as secondary antibodies, and allowed to react at a room temperature for 1 hour. After treated with the secondary antibodies, 5-minute wash with PBS was repeated for 3 times. Then, they were treated with 1 to 2 µg/mL DAPI (Sigma) for 10 minutes, and washed with PBS.

Then, the proportion (%) of C-peptide positive cells or insulin positive cells was determined using an image analyzer CellInsight (Thermo Fisher Scientific). Results are shown in FIG. 3.

Figure 3:
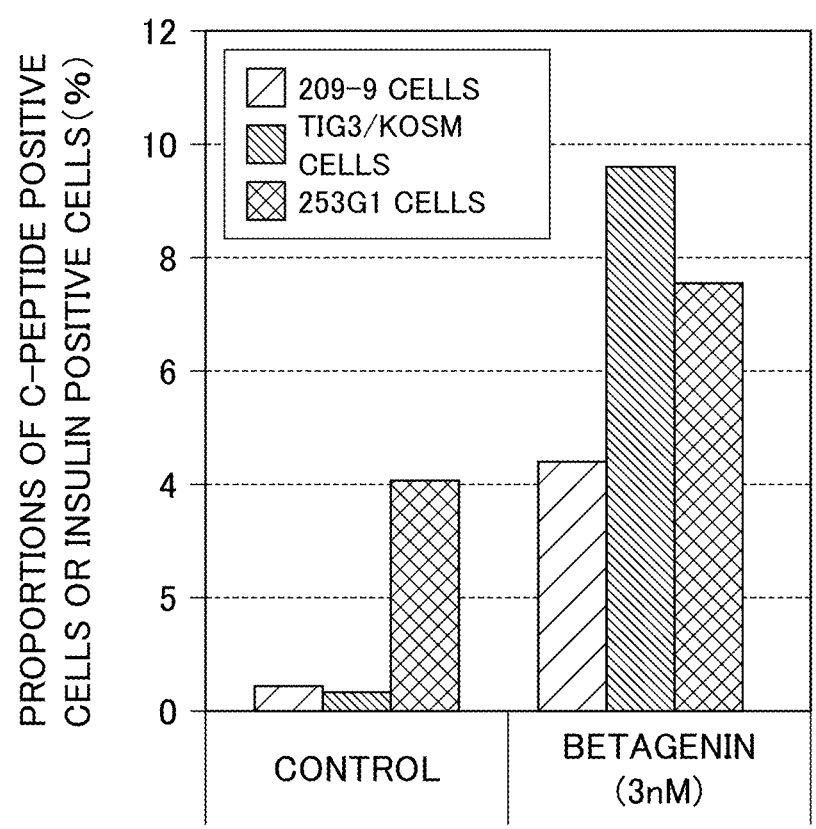
FIG. 3 shows proportions of C-peptide positive cells or insulin positive cells in cells obtained by differentiation induction when the peptide (betagenin) consisting of the amino acid sequence set forth in SEQ ID NO: 1 was added to a culture medium in the course of a differentiation induction process of human iPS cells (200-9 cells, TIG3/KOSM cells or 253G1 cells) into pancreatic hormone-producing cells.

As shown in FIG. 3, in any of the cases where 200-9 cells, TIG3/KOSM cells, 253G1 cells were used as human iPS cells, the proportion of C-peptide positive cells or insulin positive cells was increased by adding betagenin.

The results show that the differentiation induction efficiency of human iPS cells into pancreatic hormone-producing cells ($\beta$ cells) can be improved by adding betagenin to a culture medium.

Example 3: Growth Promotion of Pancreatic $\beta$ Cells (2)

MIN6 cells provided by Dr. Miyazaki at Osaka University were used as a pancreatic $\beta$ cell line. MIN6 cells were maintained in a DMEM culture medium with added 15% (v/v) of FBS.

A DMSO solution was prepared so that the concentration of chemically synthesized betagenin was 97% of purity, as a pancreatic hormone-producing cell growth-promoting agent.

Further, for comparison, an IBCAP culture supernatant and a Mock culture supernatant were prepared as follows.

First, HEK293T cells passaged in a DMEM culture medium with added 5% FBS and antibiotics (penicillin 100 U/mL, streptomycin 10 mg/mL) were plated on a 10 cm dish at 1×106 cells. On the next day, HEK293T cells were transfected with an expression vector (pCAGGS-IBCAP) constructed by ligating the gene encoding the IBCAP (=Betagenin) set forth in SEQ ID NO: 2 (which is corresponds to human TM4SF20, and hereinafter referred to "IBCAP.") using FuGEN6 (Roche) to overexpression of IBCAP. The culture medium was replaced with an Opti-MEM culture medium 24 hours after that, and a culture supernatant was then collected another 24 hours after that, which was then used as an IBCAP culture supernatant for the subsequent experiments.

Further, HEK293T cells were transfected with an empty vector (pCAGGS), and a culture supernatant was collected as described above, which was then used as a Mock culture supernatant for the subsequent experiments.

First, MIN6 cells were plated on a collagen-coated 8-well slide chamber (BD Falcon, Product Number 354630) at a cell density of 1×104 cells/well for confirming the growth promotion of pancreatic $\beta$ cells. After 24 hours, the culture medium was replaced with a DMEM culture medium with added 0.5% (v/v) of FBS, and then serum starvation was performed for 72 hours. Note that the culture medium was replaced with a fresh culture medium 48 hours after the start of serum starvation. Then, a DMSO solution of betagenin was added to the culture medium 72 hours after the start of serum starvation so that the final concentration of betagenin was 1 nM.

As a control, only DMSO was added in an equivalent addition amount instead of the DMSO solution of betagenin.

Further, for comparison, instead of the DMSO solution of betagenin, an IBCAP culture supernatant or a Mock culture supernatant was added to each well at 0.5 µL.

Twenty-four hours after adding the DMSO solution of betagenin, 5-ethynyl-2'-deoxyuridine (EdU) was added to a final concentration of 10 µM, and cultured for 2 hours. Then, cell proliferation assay was performed using a Click-iT™ Edu Alexa Flour™ 594 Imaging Kit in accordance with the accompanying instruction (Invitrogen, Product Number C10339).

Figure 4:
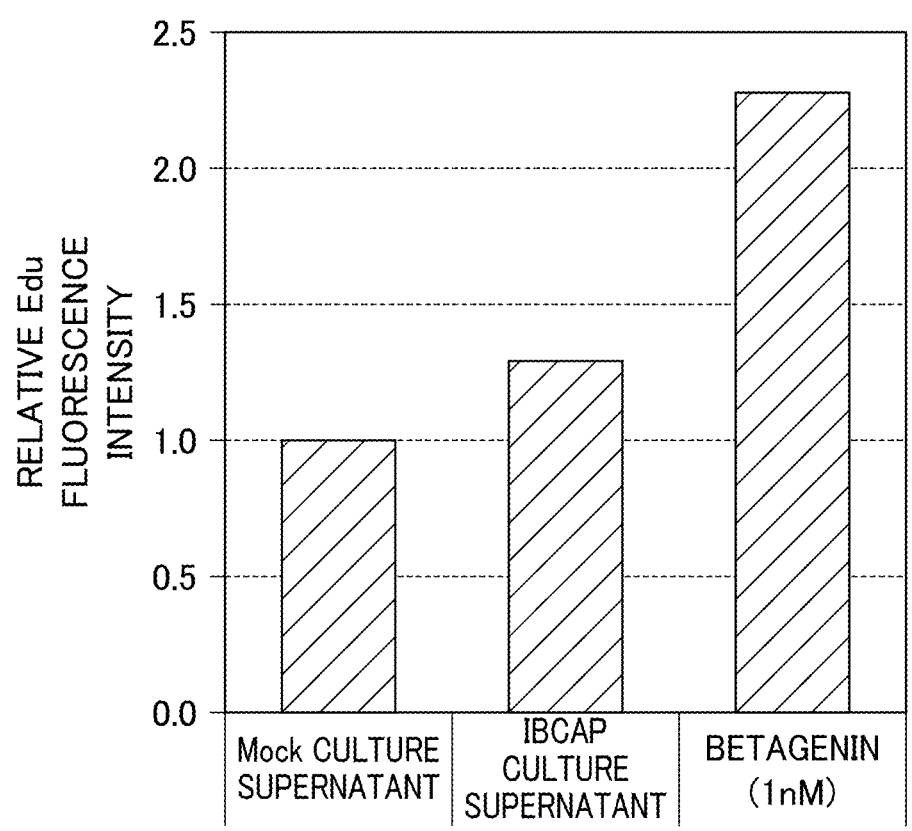
FIG. 4 shows growth-promoting activities for a pancreatic β cell line when the peptide (betagenin) consisting of the amino acid sequence set forth in SEQ ID NO: 1, a culture supernatant (IBCAP culture supernatant) of HEK293T cells transfected with an expression vector constructed by ligating the gene encoding the IBCAP (=Betagenin) set forth in SEQ ID NO: 2 or a culture supernatant (Mock culture supernatant) of HEK293T cells transfected with an empty vector was added to a culture medium.

The incorporated EdU was visualized as red fluorescence using Alexa Flour™ 594, and observed with a fluorescence microscope (Carl Zeiss). FIG. 4 shows the relative EdU fluorescence intensities obtained by subtracting the fluorescence intensity for the control from the fluorescence intensities when DMSO solution of betagenin, the IBCAP culture supernatant, the Mock culture supernatant were added, and by taking the fluorescence intensity when the Mock culture supernatant was added as 1.0.

As shown in FIG. 4, in a case where betagenin was added, the relative EdU fluorescence intensity was significantly increased as compared with a case where the IBCAP culture supernatant, the Mock culture supernatant were added.

The results show that the growth of MIN6 cells is more significantly promoted in a case where betagenin is added to the culture medium than a case where the IBCAP culture supernatant, the Mock culture supernatant are added.

Example 4: Growth Promotion of Pancreatic β Cells (3)

MIN6 cells provided by Dr. Miyazaki at Osaka University were used as a pancreatic β cell line. MIN6 cells were maintained in a DMEM culture medium with added 15% (v/v) of FBS.

A DMSO solution was prepared so that the concentration of chemically synthesized betagenin was 97% of purity, as a pancreatic hormone-producing cell growth-promoting agent.

Further, for comparison, Peptides A, B, C consisting of the amino acid sequences set forth in SEQ ID Nos: 4 to 6, respectively, were prepared by chemical synthesis.

First, MIN6 cells were plated on a collagen-coated 8-well slide chamber (BD Falcon, Product Number 354630) at a cell density of 1×104 cells/well for confirming the growth promotion of pancreas β cells. After 24 hours, the culture medium was replaced with a DMEM culture medium with added 0.5% (v/v) of FBS, and then serum starvation was performed for 72 hours. Note that the culture medium was replaced with a fresh culture medium 48 hours after the start of serum starvation. Then, a DMSO solution of betagenin was added to the culture medium 72 hours after the start of serum starvation so that the final concentration of betagenin was 1 nM.

As a control, only DMSO was added in an equivalent addition amount instead of the DMSO solution of betagenin.

Further, for comparison, instead of the DMSO solution of betagenin, Peptides A, B and C were added so that the final concentrations were 3 nM or 5 nM.

Twenty-four hours after adding the DMSO solution of betagenin or Peptides A, B, C, 5-ethynyl-2'-deoxyuridine (EdU) was added to a final concentration of 10 µM, and cultured for 2 hours. Then, cell proliferation assay was performed using a Click-iT™ Edu Alexa Flour™ 594 Imaging Kit in accordance with the accompanying instruction (Invitrogen, Product Number C10339).

Figure 5:
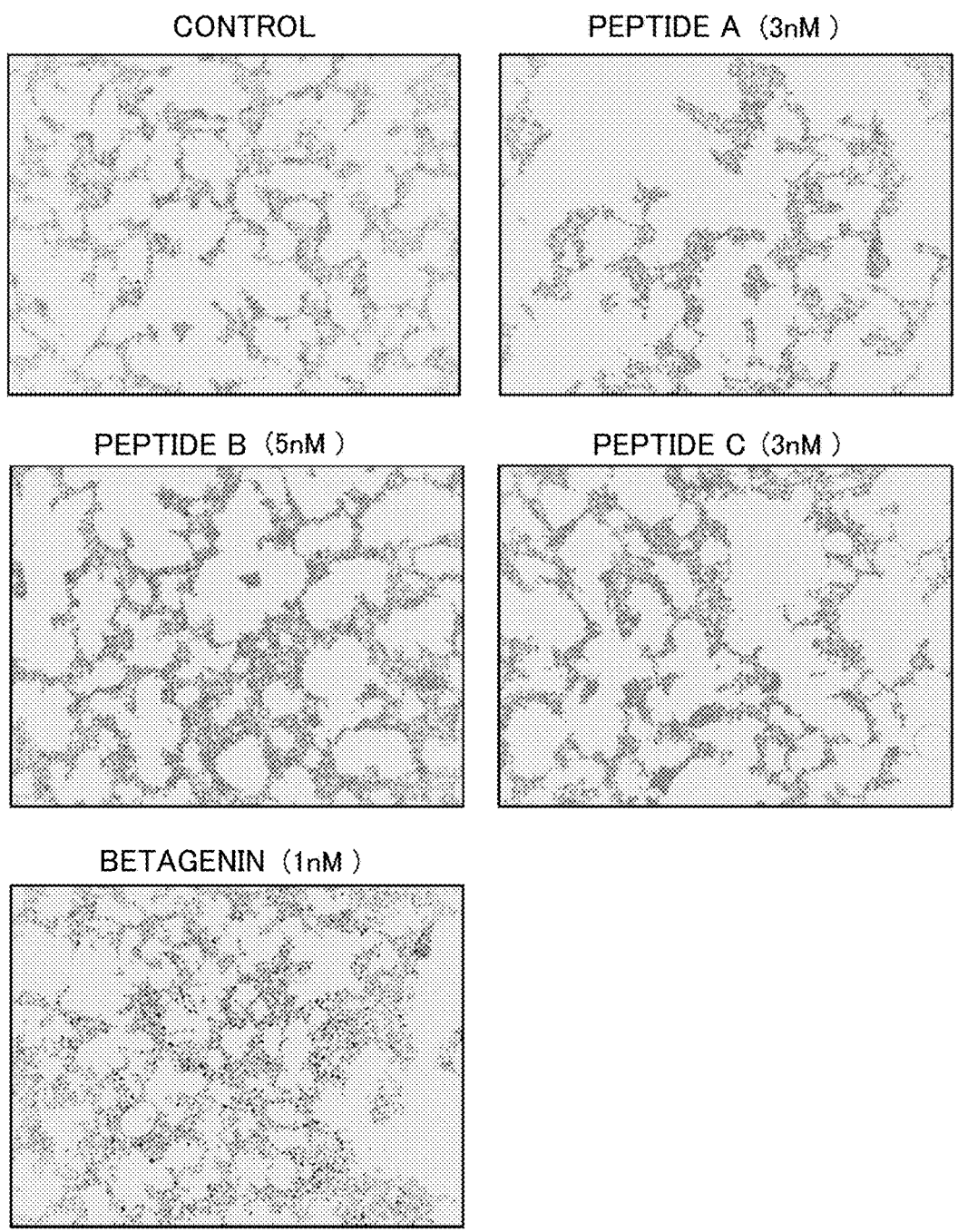
FIG. 5 shows growth-promoting activities for a pancreatic β cell line when the peptide (betagenin) consisting of the amino acid sequence set forth in SEQ ID NO: 1 or the peptides (Peptides A, B, C) consisting of the amino acid sequence set forth in SEQ ID NOs: 4 to 6 was added to a culture medium.

The incorporated EdU was visualized as red fluorescence using Alexa Flour™ 594, and observed with a fluorescence microscope (Carl Zeiss). FIG. 5 shows fluorescence microscope images subjected to black and white processing followed by black and white inversion. Note that a red fluorescence part representing a region where EdU was taken up will be confirmed as a dark black part due to the operations of black and white processing and black and white inversion.

As shown in FIG. 5, in a case where betagenin was added, significantly darker black parts were observed as compared with a case where Peptide A, B, C were added.

The results shows that the growth of MIN6 cells is significantly more promoted when betagenin is added as compared with when Peptides A, B, C are added although betagenin and Peptides A, B, C are all fragments of human TM4SF20.

Example 5: Differentiation Induction of Human iPS Cells into Pancreatic Hormone-Producing Cells (2)

As human iPS cells, used were 253G1 cells purchased from the cell bank at RIKEN. The cells were cultured/maintained in an ES cell culture medium (DMEM/ham F12, 20% KSR, nonessential amino acid, 2 mM L-glutamine, 0.1 mM 2-mercaptoethanol, 5.2 mM NaOH) with added 4 ng/mL FGF-2 (Global Stem) and penicillin/streptomycin (Nacalai Tesque, Inc.) along with SNL76/7 cells (DS Pharma Biomedical) treated with mitomycin-C. CTK (0.25% trypsin, 1 mg/mL Collagenase IV, 20% KSR, 1 mM CaCl2 in PBS) was used for cell detachment, and diluted at a ratio of 1:3 to 1:4 to perform passage culture.

The cells were detached with trypsin-EDTA 3 days before the start of differentiation induction, and plated at a cell density of 6.3×104 cells/cm2, and cultured for 1 day in an ES cell culture medium with added 10 µM Y-27632 (Wako), 4 ng/mL FGF-2 and penicillin/streptomycin along with STO cells treated with mitomycin-C. Subsequently, they were further cultured for 2 days in an ES cell culture medium with added 4 ng/mL FGF-2 and penicillin/streptomycin.

On the first day of the start of differentiation induction, the culture medium was replaced with a RPMI1640 culture medium (Nacalai Tesque, Inc.) with added 2% (v/v) FBS, 100 ng/mL activin A (SBI), 3 µM CHIR99021 (Axon Medchem) and 1 nM betagenin, and cultured for 1 day (Step (A2)).

Subsequently, the culture medium was replaced with a RPMI1640 culture medium with added 2% (v/v) FBS, 100 ng/mL activin A and 1 nM betagenin, and cultured for 2 days (Step (B2)).

Then, the culture medium was replaced with an IMEM Zinc Option culture medium (Gibco) with added 1% (v/v) B-27TM supplement (Invitrogen), 1 µM dorsomorphin (Calbiiochem), 2 µM retinoic acid (Sigma), 10 µM SB431542 (Sigma) and 1 nM betagenin, and cultured for 7 days (Step (C2)).

Finally, the culture medium was replaced with an IMEM Zinc Option culture medium with added 1% (v/v) B-27TM supplement, 10 µM forskolin (Wako), 10 µM dexamethasone (Wako), 5 µM Alk5 inhibitor II (Calbiochem), 10 µM nicotinamide (Wako) and 1 nM betagenin, and cultured for 11 days (Step (D2)). As a control, acetonitrile (ACN), which was a solvent for betagenin, was added at an equivalent addition amount.

(Quantitative RT-PCR Analysis)

The gene expressions of insulin, glucagon, somatostatin were confirmed by quantitative RT-PCR for cells (n=3 for each of the betagenin addition group and the control group) obtained from 253G1 cells via the above steps (A2) to (D2). Specifically, total RNA was first extracted from the cells using a SV Total RNA Isolation System (Promega), and reverse transcription reactions were performed with BioScript™ transcriptase (Bioline), and then quantitative PCR analysis was performed with LightCycler™ (Roche) using SYBR™ Green PCR Master Mix (Applied Biosystems).

Note that the gene expression of GAPDH was determined by quantitative RT-PCR as an internal control. Primer sequences are shown below.

```
HsINS_31F:     GCCATCAAGCAGATCACTGT   (SEQ ID NO: 7)

HsINS_149R:    CAGGTGTTGGTTCACAAAGG   (SEQ ID NO: 8)

HsGCG_264F:    GCATTTACTTTGTGGCTGGA   (SEQ ID NO: 9)

HsGCG_368R:    CCTGGGAAGCTGAGAATGAT   (SEQ ID NO: 10)

HsSST_206F:    CCCCAGACTCCGTCAGTTTC   (SEQ ID NO: 11)

HsSST_313R:    TCCGTCTGGTTGGGTTCAG    (SEQ ID NO: 12)

hGAPDH-F:      ATGTTCGTCATGGGTGTGAA   (SEQ ID NO: 13)

hGAPDH-R:      TGTGGTCATGAGTCCTTCCA   (SEQ ID NO: 14)
```

PCR products were separated by 3% agarose gel electrophoresis, and visualized with ethidium bromide, BioDoc-It Imaging System (BMbio).

Figure 6:
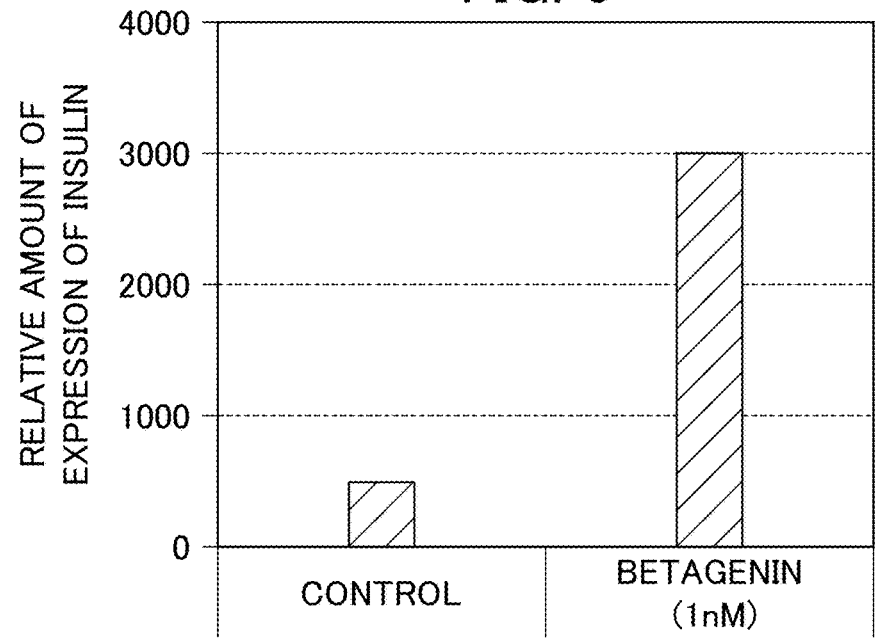
FIG. 6 shows relative expression amounts of insulin in cells obtained by differentiation induction when the peptide (betagenin) consisting of the amino acid sequence set forth in SEQ ID NO: 1 was added to a culture medium in the course of a differentiation induction process of human iPS cells (253G1 cells) into pancreatic hormone-producing cells.
Figure 7:
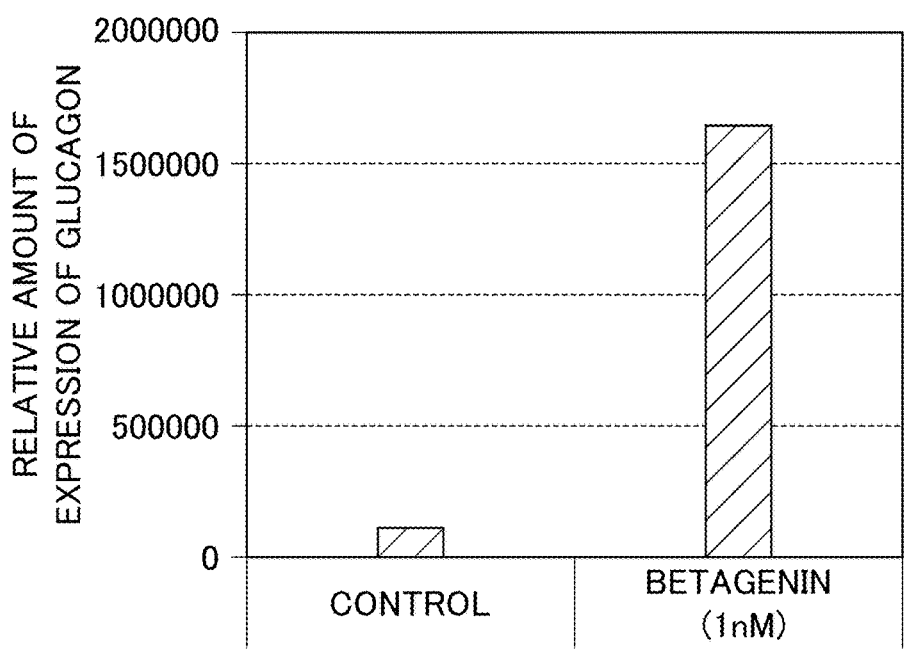
FIG. 7 shows relative expression amounts of glucagon in cells obtained by differentiation induction when the peptide (betagenin) consisting of the amino acid sequence set forth in SEQ ID NO: 1 was added to a culture medium in the course of a differentiation induction process of human iPS cells (253G1 cells) into pancreatic hormone-producing cells.
Figure 8:
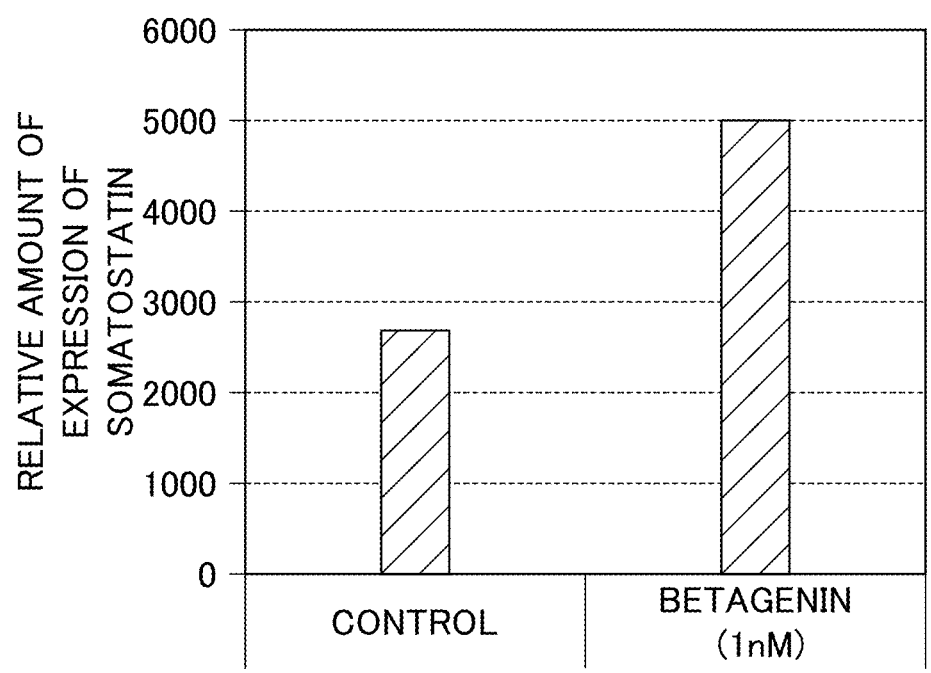
FIG. 8 shows relative expression amounts of somatostatin in cells obtained by differentiation induction when the peptide (betagenin) consisting of the amino acid sequence set forth in SEQ ID NO: 1 was added to a culture medium in the course of a differentiation induction process of human iPS cells (253G1 cells) into pancreatic hormone-producing cells.

The amounts of expression of insulin, glucagon, somatostatin in the cells obtained via the step (D2) are shown in FIGS. 6 to 8, respectively. FIGS. 6 to 8 show the relative amounts of expression when correction was performed with the GAPDH gene, and the amounts of expression of insulin, glucagon, somatostatinin in the cells on the first day of differentiation induction are taken as 1.

As shown in FIGS. 6 to 8, the amounts of expression of insulin, glucagon, somatostatin were increased by adding betagenin.

The results show that the differentiation induction efficiency of human iPS cells into pancreatic hormone-producing cells (α cells, β cells, δ cells) can be improved by adding betagenin to a culture medium.

SEQUENCE LIST idennsi2014.5.23.txt

The invention claimed is:

1. A peptide consisting of the amino acid sequence set forth in SEQ ID NO: 1.

2. A research reagent comprising the peptide according to claim 1, wherein the research reagent is a pancreatic hormone-producing cell growth-promoting agent for promoting the growth of pancreatic hormone-producing cells and/or a differentiation-induction promoting agent for inducing differentiation into pancreatic hormone-producing cells.

3. The research reagent according to claim 2, wherein the pancreatic hormone-producing cells comprise at least one selected from the group consisting of α cells, β cells and δ cells.

4. A pharmaceutical composition comprising the peptide according to claim 1.

5. A pancreatic hormone-producing cell growth-promoting agent for promoting the growth of pancreatic hormone-producing cells, comprising:
   a peptide consisting of the amino acid sequence set forth in SEQ ID NO: 1.

6. A differentiation-induction promoting agent for inducing differentiation into pancreatic hormone-producing cells, comprising:
   a peptide consisting of the amino acid sequence set forth in SEQ ID NO: 1.

* * * * *

SEQUENCE LISTING

```
<160> NUMBER OF SEQ ID NOS: 14

<210> SEQ ID NO 1
<211> LENGTH: 60
<212> TYPE: PRT
<213> ORGANISM: Homo sapiens
<220> FEATURE:
<223> OTHER INFORMATION: Peptide Sequence betagenin

<400> SEQUENCE: 1

Trp Arg Ala Ser Ser Phe His Phe Asp Ser Glu Glu Asn Lys His Arg
1               5                   10                  15

Leu Ile His Phe Ser Val Phe Leu Gly Leu Leu Val Gly Ile Leu
            20                  25                  30

Glu Val Leu Phe Gly Leu Ser Gln Ile Val Ile Gly Phe Leu Gly Cys
            35                  40                  45

Leu Cys Gly Val Ser Lys Arg Arg Ser Gln Ile Val
    50                  55                  60

<210> SEQ ID NO 2
<211> LENGTH: 2308
<212> TYPE: DNA
<213> ORGANISM: Homo sapiens

<400> SEQUENCE: 2
aagccacttt gacaacgttt ctgagccagg ggtgaccatg acctgctgcg aaggatggac    60
atcctgcaat ggattcagcc tgctggttct actgctgtta ggagtagttc tcaatgtgat   120
acctctaatt gtcagcttag ttgaggaaga ccaatttttct caaaacccca tctcttgctt   180
tgagtggtgg ttcccaggaa ttataggagc aggtctgatg gccattccag caacaacaat   240
gtccttgaca gcaagaaaaa gagcgtgctg caacaacaga actggaatgt ttctttcatc   300
acttttcagt gtgatcacag tcattggtgc tctgtattgc atgctgatat ccatccaggc   360
tctcttaaaa ggtcctctca tgtgtaattc tccaagcaac agtaatgcca attgtgaatt   420
ttcattgaaa aacatcagtg acattcatcc agaatccttc aacttgcagt ggttttttcaa   480 tgactcttgt gcacctccta ctggtttcaa taaacccacc agtaacgaca ccatggcgag   540
tggctggaga gcatctagtt tccacttcga ttctgaagaa aacaaacata ggcttatcca   600
cttctcagta tttttaggtc tattgcttgt tggaattctg gaggtcctgt ttgggctcag   660
```

-continued

```
tcagatagtc atcggtttcc ttggctgtct gtgtggagtc tctaagcgaa gaagtcaaat      720
tgtgtagttt aatgggaata aaatgtaagt atcagtagtt tgaattaatt tgagaagtac      780
acttgttttc aaagtcatct ttgagatgat ttaaaaaatc aacccttcac gtagaaagca      840
cgttgtaaat gcataacact ctcatatcag tggttgattt gggaaaggtg gagagaattt      900
tcaattagtt ttgtgttgta ctattcaaat tttttacctc ttcactgtgt gtagagaaag      960
gagaagggaa ggaggatgag aaggaacgga agtcatcctg aaaataaaag tacaggactt     1020
tttttttttt tttttgagac agggtctcaa aaaaggctgg agtacagtag tacagtggtg     1080
ctatctcagc ttactgcagc ctcaacctcc tgggctcagg tgattctccc atctcagcct     1140
ccctagtagc tgggactaca ggtgcgtgcc actatgccaa gctaattttt gtatttttag     1200
tagagatggg ggttttccat attgcccagg ctggtcccga actcatggac tcaagtgatc     1260
tgcctgcctc agcctcctaa agtgctgcga ttacaggcat gagccatcgc gcctaaagga     1320
caggaccttt ttattgtatt tctttaaaga ataaatacat aacctgaatg caatcaagtc     1380
tttagatcta attctcagct tgcagggaac actaggacaa atccaaaaag tgggtcagcg     1440
ggcacagaat ggcccaattt tcaacaggaa atgttataa agaaaaata ttttgaggg      1500 aactgttata gattaagaga atagaggcat gtttcagcta acacatgta aactttgtca       1560 gagataattg ggaggagtat gtagaagaat cggattattg ttaattttgg taggtctgat     1620
aatggtttta tagtataaag gctgagtacc cctatccaa atgattaag atcagaagtg       1680 ttttggcttt cacattttt tggattttgg aattttgcct ataataatga gacatcttgg      1740
ggatgggatg caagtctaac cacaaaattc atttatgtct catacacact ttgaacacct     1800
ggcctgaagg taatttcaca caatatttta ataactttg tgcatgaaac acaattttga      1860
ctgcattttg actgcaactc atcacatgag gtcaggtatg gaattttcca cttgtggtgt     1920
tacgttactg gctcaaaaag ttttggatct cggagcattc tggattttga attttggat     1980 tagtgatgct caacctgtat acagaaatgt cctcattttt aaaaaagaa atgcatattt      2040 atatgtttta aaattacttc aaccaaaagc aacggggaga tgtttactgt tatatttagg     2100
tgacaggtac atggcaattc attataccct cctattttcc tatgtttaca ttattcatta    2160
attaaaaaac aatacctaga aaacccaag actttcaaaa gctattttct atatgtgcca      2220
atctttaaaa aacaggataa caagggtatt tatcacatta aaatgttgta aaacagcaaa     2280
gctaaaatct aaaaaaaaaa aaaaaaaa                                         2308
```

<210> SEQ ID NO 3
<211> LENGTH: 229
<212> TYPE: PRT
<213> ORGANISM: Homo sapiens

<400> SEQUENCE: 3

Met Thr Cys Cys Glu Gly Trp Thr Ser Cys Asn Gly Phe Ser Leu Leu
1               5                   10                  15

Val Leu Leu Leu Leu Gly Val Val Leu Asn Val Ile Pro Leu Ile Val
            20                  25                  30

Ser Leu Val Glu Glu Asp Gln Phe Ser Gln Asn Pro Ile Ser Cys Phe
        35                  40                  45

Glu Trp Trp Phe Pro Gly Ile Ile Gly Ala Gly Leu Met Ala Ile Pro
    50                  55                  60

Ala Thr Thr Met Ser Leu Thr Ala Arg Lys Arg Ala Cys Cys Asn Asn
65                  70                  75                  80

```
Arg Thr Gly Met Phe Leu Ser Ser Leu Phe Ser Val Ile Thr Val Ile
                85                  90                  95

Gly Ala Leu Tyr Cys Met Leu Ile Ser Ile Gln Ala Leu Leu Lys Gly
            100                 105                 110

Pro Leu Met Cys Asn Ser Pro Ser Asn Ser Asn Ala Asn Cys Glu Phe
        115                 120                 125

Ser Leu Lys Asn Ile Ser Asp Ile His Pro Glu Ser Phe Asn Leu Gln
    130                 135                 140

Trp Phe Phe Asn Asp Ser Cys Ala Pro Pro Thr Gly Phe Asn Lys Pro
145                 150                 155                 160

Thr Ser Asn Asp Thr Met Ala Ser Gly Trp Arg Ala Ser Ser Phe His
                165                 170                 175

Phe Asp Ser Glu Glu Asn Lys His Arg Leu Ile His Phe Ser Val Phe
            180                 185                 190

Leu Gly Leu Leu Leu Val Gly Ile Leu Glu Val Leu Phe Gly Leu Ser
        195                 200                 205

Gln Ile Val Ile Gly Phe Leu Gly Cys Leu Cys Gly Val Ser Lys Arg
    210                 215                 220

Arg Ser Gln Ile Val
225

<210> SEQ ID NO 4
<211> LENGTH: 19
<212> TYPE: PRT
<213> ORGANISM: Homo sapiens

<400> SEQUENCE: 4

Ala Leu Tyr Cys Met Leu Ile Ser Ile Gln Ala Leu Leu Lys Gly Pro
1               5                   10                  15

Leu Met Cys

<210> SEQ ID NO 5
<211> LENGTH: 19
<212> TYPE: PRT
<213> ORGANISM: Homo sapiens

<400> SEQUENCE: 5

Cys Asn Asn Arg Thr Gly Met Phe Leu Ser Ser Leu Phe Ser Val Ile
1               5                   10                  15

Thr Val Ile

<210> SEQ ID NO 6
<211> LENGTH: 19
<212> TYPE: PRT
<213> ORGANISM: Homo sapiens

<400> SEQUENCE: 6

Thr Ser Asn Asp Thr Met Ala Ser Gly Trp Arg Ala Ser Ser Phe His
1               5                   10                  15

Phe Asp Ser

<210> SEQ ID NO 7
<211> LENGTH: 20
<212> TYPE: DNA
<213> ORGANISM: Artificial sequence
<220> FEATURE:
<223> OTHER INFORMATION: Synthesized oligonucleotide
```

<400> SEQUENCE: 7
gccatcaagc agatcactgt                                                    20

<210> SEQ ID NO 8
<211> LENGTH: 20
<212> TYPE: DNA
<213> ORGANISM: Artificial sequence
<220> FEATURE:
<223> OTHER INFORMATION: Synthesized oligonucleotide

<400> SEQUENCE: 8
caggtgttgg ttcacaaagg                                                    20

<210> SEQ ID NO 9
<211> LENGTH: 20
<212> TYPE: DNA
<213> ORGANISM: Artificial sequence
<220> FEATURE:
<223> OTHER INFORMATION: Synthesized oligonucleotide

<400> SEQUENCE: 9
gcatttactt tgtggctgga                                                    20

<210> SEQ ID NO 10
<211> LENGTH: 20
<212> TYPE: DNA
<213> ORGANISM: Artificial sequence
<220> FEATURE:
<223> OTHER INFORMATION: Synthesized oligonucleotide

<400> SEQUENCE: 10
cctgggaagc tgagaatgat                                                    20

<210> SEQ ID NO 11
<211> LENGTH: 20
<212> TYPE: DNA
<213> ORGANISM: Artificial sequence
<220> FEATURE:
<223> OTHER INFORMATION: Synthesized oligonucleotide

<400> SEQUENCE: 11
ccccagactc cgtcagtttc                                                    20

<210> SEQ ID NO 12
<211> LENGTH: 19
<212> TYPE: DNA
<213> ORGANISM: Artificial sequence
<220> FEATURE:
<223> OTHER INFORMATION: Synthesized oligonucleotide

<400> SEQUENCE: 12
tccgtctggt tgggttcag                                                     19

<210> SEQ ID NO 13
<211> LENGTH: 20
<212> TYPE: DNA
<213> ORGANISM: Artificial sequence
<220> FEATURE:
<223> OTHER INFORMATION: Synthesized oligonucleotide

<400> SEQUENCE: 13
atgttcgtca tgggtgtgaa                                                    20

```
<210> SEQ ID NO 14
<211> LENGTH: 20
<212> TYPE: DNA
<213> ORGANISM: Artificial sequence
<220> FEATURE:
<223> OTHER INFORMATION: Synthesized oligonucleotide

<400> SEQUENCE: 14
tgtggtcatg agtccttcca                                              20
```